(12) United States Patent
Jackson et al.

(10) Patent No.: US 7,538,233 B2
(45) Date of Patent: May 26, 2009

(54) COUMARINS AS INOS INHIBITORS

(75) Inventors: Sharon Jackson, Whitehouse Station, NJ (US); Thaddeus Nieduzak, Bridgewater, NJ (US); Sam Rebello, Bridgewater, NJ (US); Guyan Liang, Warren, NJ (US); Yulin Chiang, Convent Station, NJ (US); Jean Merrill, Whippany, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 444 days.

(21) Appl. No.: 10/925,292

(22) Filed: Aug. 24, 2004

(65) Prior Publication Data

US 2005/0054681 A1    Mar. 10, 2005

Related U.S. Application Data

(60) Provisional application No. 60/500,610, filed on Sep. 5, 2003.

(51) Int. Cl.
*C07D 311/02*    (2006.01)
*A61K 31/35*    (2006.01)

(52) U.S. Cl. .................................. 549/285; 514/457

(58) Field of Classification Search ................ 514/451; 549/285, 283

See application file for complete search history.

(56) References Cited

U.S. PATENT DOCUMENTS

| | | |
|---|---|---|
| 3,515,721 A | 6/1970 | Heinrich et al. |
| 3,784,600 A | 1/1974 | Strandtmann et al. |
| 4,210,667 A | 7/1980 | Sarges et al. |
| 4,230,850 A | 10/1980 | Briet et al. |
| 5,247,099 A | 9/1993 | Celebuski |
| 5,342,970 A | 8/1994 | Chalom et al. |
| 5,412,104 A | 5/1995 | Afonso et al. |
| 5,424,320 A | 6/1995 | Fortin et al. |
| 5,554,611 A | 9/1996 | Schonafinger et al. |
| 5,646,164 A | 7/1997 | Tzeng et al. |
| 5,716,983 A | 2/1998 | Friebe et al. |
| 5,962,460 A | 10/1999 | Tzeng et al. |
| 5,998,593 A | 12/1999 | Huff et al. |
| 6,008,008 A | 12/1999 | James et al. |
| 6,034,121 A | 3/2000 | O'Mahony et al. |
| 6,143,766 A | 11/2000 | Kaltenbronn et al. |

FOREIGN PATENT DOCUMENTS

| | | | |
|---|---|---|---|
| FR | 2711992 A1 * | 3/1993 | |
| WO | WO 94/12488 | 6/1994 | |
| WO | WO 97/41138 | 11/1997 | |
| WO | WO 99/21550 | 5/1999 | |

OTHER PUBLICATIONS

Majumdar, K.C. et al Tetrahedron 2003, 59, 2151-2157.*
Haywood, D.J. et al 1979, 28, 2637-2638.*
Hanmantgad, S. et al Indian Journal of Chemistry 1985, 24B, 459-461.*
A. K. Panigrahi et al., Antispasmodics Derived From Substituted 4-Hydroxy Coumarine, Jour. & Proc. Inst. Chem. (1966, pp. 171-174, vol. XXXVIII).
C. Antonello et al., Diethylaminoalkyloxycoumarin And -Furocoumarin Derivatives, IL Farmaco Ed. Sc. (1978, pp. 139-156, vol. 34, No. 2).
Cipriano Antonello et al., Derivati Dietilamminoalcossilici Di Cumarine E Furocumarine, Atti Dell'Lstituto Veneto Di Scienze, Lettere Ed Arti (1976-77, pp. 17-35).
David Crich et al., Generation And Cyclization Of Acyl Radicals From Thiol Esters Under Nonreducing, Tin-Free Conditions, J. Org. Chem. (1997, pp. 5982-5988, vol. 62).
Dimitra J. Hadjipavlou-Litina, New Diaminoether Coumarinic Derivatives with Anti-Inflammatory Activity, Arzneim-Forsch./Drug Res. (2000, pp. 631-635, vol. 50, No. 7).
Harumasa Totani et al., Coumarin Derivatives As Human Immunodeficiency Virus Inhibitors, Abstract.
Jie Wu et al., Synthesis of 4-Substituted Coumarines via the Palladium Cross-Couplings of 4-Tosylcoumarins with Terminal Acetylenes And Organozinc Reagents, J. Org. Chem (2001, pp. 3642-3645, vol. 66).
Kazuo Nagasawa et al., Coumarins-Containing Amino Acids And Oxy Acids As Chiral Discriminating Agents. Part III. Novel Crystalline (R)-(+)- And (S)-(−)-O-Coumarininyl Lactic Acibs As Chiral Derivatizing Agents For 1N NMR Inspection Of Optical Purities Of Alcohols and Amines, Heterocycles (1997, pp. 567-580, vol. 46).
Laurent Schio et al., Tosylates In Palladium-Catalysed Coupling Reactions. Application To The Synthesis Of Arylcoumarin Inhibitors Of Gyrase B, Tetrahedron Letters (2000, pp. 1543-1547, vol. 41).
Patrick Vallance et al., Blocking No Synthesis: How, Where and Why?, Nature Reviews (2002, pp. 939-950, vol. 1).

(Continued)

*Primary Examiner*—Rita J Desai
*Assistant Examiner*—John Mabry
(74) *Attorney, Agent, or Firm*—Joseph Strupczewski; Craig M. Bell

(57) ABSTRACT

The present invention relates to coumarins of the formula (I):

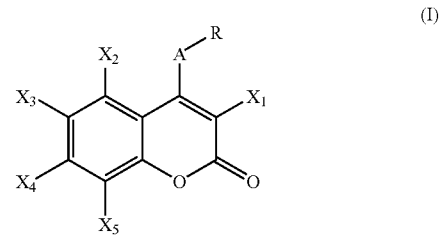

that are useful as inhibitors of nitric oxide synthase. Pharmaceutical compositions and methods of using these compounds as inhibitors of nitric oxide synthase are described herein.

7 Claims, No Drawings

OTHER PUBLICATIONS

V. A. Zagorevskii et al., A New Type Of Transformation Of 4-Chlorocoumarin, Abstract (1962, pp. 2383-2384, vol. 32).

V. A. Zagorevskii et al., Pyran Series, its Analogs, And Related Compounds. XXXV. Reaction of 4-Chlorocoumarin and Sodium Alcoholates, Abstract.

Maciej Adamczyk et al., Novel 7-Hydroxycoumarin Based Fluorescent Labels, Bioorganic & Medicinal Chemistry Letters, (1985, pp. 1985-1988, vol. 7, No. 15).

H. Akgun et al., Some New 7-Aryloxyalkyltheophyllines As Bronchodilators, Eur J. Med. Chem. (1997, pp. 175-179, vol. 32).

I. Dragota et al., Potential Anticancer Agents. XII Synthesis Of New Methanesulphonate Derivatives From Benzo-And Naphtopyrans, Revue Roumaine de Chimie, (1976, pp. 1543-1554, vol. 21, No. 11-12).

Jie Wu et al., Nickel-Catalyzed Cross-Couplings of 4-Diethylphosphonooxycoumarins with Organozinc Reagents: An Efficient new Methodology For The Synthesis Of 4-Substituted Coumarins, J. Org. Chem. (2002, pp. 7875-7878, vol. 66).

\* cited by examiner

COUMARINS AS INOS INHIBITORS

This application claims the benefit of U.S. Provisional Application No. 60/500,610 filed Sep. 5, 2003.

FIELD OF THE INVENTION

This present invention relates to preparation of certain novel coumarins of formula (I) and their use as inhibitors of inducible NO (nitric oxide) synthase (iNOS).

BACKGROUND OF THE INVENTION

Nitric oxide is an endogenous stimulator of the soluble guanylate cyclase. In addition to endothelium-dependent relaxation, NO is involved in a number of biological actions including cytotoxicity of phagocytic cells and cell-to-cell communication in the central nervous system.

Three NOS isoforms, two of which are constitutive and one inducible, are known:

(i) a neuronal NOS (NOS-1 or nNOS) is originally isolated and cloned from nerve tissue in which it is a constitutive enzyme. NOS-1 produces NO in response to various physiological stimuli such as the activation of membrane receptors according to a mechanism dependent on calcium and on calmodulin;

(ii) an inducible NOS (NOS-2 or iNOS) can be induced in response to immunological stimuli such as, for example, cytokines or bacterial antigens in various cells such as, for example, macrophages, endothelial cells, hepatocytes, glial cells, as well as many other types of cell. The activity of this isoform is not regulated by calcium. Consequently, once induced, it produces large amounts of NO over prolonged periods.

(iii) an endothelial NOS (NOS-3 or eNOS) is constitutive and calcium/calmodulin-dependent. It is originally identified in vascular endothelial cells, in which it generates NO in response to physiological stimuli such as the activation of membrane receptors.

The NO produced by the neuronal and endothelial constitutive isoforms (NOS-1 and NOS-3) is generally involved in intercellular signaling functions. For example, the endothelial cells, which line the inner wall of the blood vessels, induce the relaxation of the underlying smooth muscle cells via the production of NO. It thus contributes towards regulating the arterial pressure.

The NO produced in large amount by the inducible isoform NOS-2 is, inter alia, involved in pathological phenomena associated with acute and chronic inflammatory processes in a large variety of tissues and organs.

An excessive production of NO by induction of NOS-2 thus plays a part in degenerative pathologies of the nervous system such as, for example, multiple sclerosis, cerebral, focal or global ischemia, cerebral or spinal trauma, Parkinson's disease, Huntington's disease, Alzheimer's disease, amyotrophic lateral sclerosis, migraine, depression, schizophrenia, anxiety and epilepsy. Similarly, aside from the central nervous system, the induction of NOS-2 is involved in numerous pathologies with inflammatory components, such as, for example, diabetes, atherosclerosis, myocarditis, arthritis, arthrosis, asthma, irritable bowel syndrome, Crohn's disease, peritonitis, gastro-esophageal reflux, uveitis, Guillain-Barre syndrome, glomerulonephritis, lupus erythematosus and psoriasis. NOS-2 has also been implicated in the growth of certain forms of tumors such as, for example, epitheliomas, adenocarcinomas or sarcomas, and in infections with Gram-positive or Gram-negative intracellular or extracellular bacteria.

In all the situations in which an overproduction of NO is deleterious, it thus appears to be desirable to reduce the production of NO by administering substances capable of inhibiting NOS-2. However, given the important physiological roles played by the constitutive isoform NOS-3, in particular in regulating arterial pressure, it is of fundamental importance that the inhibition of the isoform NOS-2 should have the least possible effect on the isoform NOS-3. The reason for this is that it is known that the administration of unselective inhibitors of the NOS isoforms leads to vasoconstriction and an increase in arterial pressure (Moncada, S., *Biochem. Pharmacol.*, 1989, 38: 1709-1715). These effects on the cardiovascular system are deleterious since they reduce the supply of nutrients to the tissues. Consequently, the present invention relates to compounds whose inhibitory activity with respect to NOS-2 is significantly higher than their inhibitory activity with respect to NOS-3.

SUMMARY OF THE INVENTION

The present invention is a compound of formula (I)

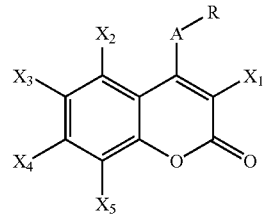

wherein:
A is O or a bond;
when A is O, R is selected from the group consisting of $C_{1-6}$alkylsulfonyl, cyano$C_{1}$-$C_{6}$alkyl, carboxy$C_{1}$-$C_{6}$alkyl, hydroxy $C_{1}$-$C_{6}$alkyl, $C_{1}$-$C_{6}$alkoxycarbonyl$C_{3}$-$C_{8}$cycloalkyl$C_{1}$-$C_{6}$alky, carboxy$C_{3}$-$C_{8}$cycloalkyl$C_{1}$-$C_{6}$alky, aryl$C_{1}$-$C_{6}$alkyl, heteroaryl$C_{1}$-$C_{6}$alkyl, heterocyclyl, heterocyclyl$C_{1}$-$C_{6}$alkyl, heterocyclyloxy$C_{1}$-$C_{6}$alkyl, heteroarylsulfonyl, wherein aryl, heteroaryl and heterocyclyl are optionally substituted with one or two substituents each independently selected from $C_{1-6}$alkyl, $C_{1-6}$alkoxy, halogen, hydroxy or $C_{1-6}$perfluoroalkyl or $C_{1-6}$perfluoroalkoxy and $(CH_2)_n NR_1R_2$, wherein $R_1$ $R_2$ are the same or different and are selected from, the group consisting of hydrogen, $C_1$-$C_6$ alkyl, $C_{2-6}$alkenyl, $C_{2-6}$alkynyl, $C_{1-6}$perfluoroalkyl, $C_{3-8}$cycloalkyl, $C_{3-8}$cycloalkyl$C_{1-6}$alkyl, $C_{16}$alkoxy$C_{1-6}$alkyl, hydroxy$C_{1-6}$alkyl, amino$C_{1-6}$alkyl, mono- or di-$C_{1-6}$alkyl-amino$C_{1-6}$alkyl, formyl, $C_{3-8}$alkylcarbonyl, amino$C_{1-6}$alkylcarbonyl, $C_{1-6}$alkoxycarbonyl, $C_{1-6}$alkylsulfonyl, $C_{1-6}$alkylaminothiocarbonyl, aryl, diphenyl$C_{1-6}$alkyl and aryl$C_{1-6}$alkyl, arylcarbonyl$C_{1-6}$ alkyl, aryloxy$C_{1-6}$alkyl, C(=NH)NH$_2$; COOR$_3$ and, wherein R$_3$ is $C_1$-$C_6$ alkyl, wherein aryl is optionally substituted with one or two substituents each independently selected from $C_{1-6}$alkyl, $C_{1-6}$alkoxy, halogen, hydroxy or $C_{1-6}$perfluoroalkyl or $C_{1-6}$perfluoroalkoxy;
when A is a bond, R is selected from the group consisting of carboxy $C_{1-C6}$alkyl, aminocarbonyl$C_{1}$-$C_{6}$alkyl, cyanoC$_1$-C$_6$alkyl and (CH$_2$)$_n$NHR$_1$, wherein R$_1$ is selected from, the group consisting of hydrogen, C$_1$-C$_6$alkyl, C$_{2-6}$alkenyl, C$_{2-6}$alkynyl, C$_{1-6}$perfluoroalkyl, C$_{3-8}$cycloalkyl, C$_{3-8}$cycloalkylC$_{1-6}$alkyl, C$_{1-6}$alkoxyC$_{1-6}$alkyl, hydroxyC$_{1-6}$alkyl, aminoC$_{1-6}$alkyl, mono- or di-C$_{1-6}$alkyl-aminoC$_{1-6}$alkyl, formyl, C$_{1-6}$alkylcarbonyl, aminoC$_{1-6}$alkylcarbonyl, C$_{1-6}$alkoxycarbonyl, C$_{1-6}$alkylsulfonyl, C$_{1-6}$alkylaminothiocarbonyl, aryl, diphenylC$_{1-6}$alkyl and arylC$_{1-6}$alkyl, arylcarbonylC$_{1-6}$alkyl, heteroarylcarbonyl, aryloxyC$_{1-6}$alkyl, CNHNH$_2$ and COOR$_3$, wherein R$_3$ is C$_1$-C$_6$ alkyl, wherein aryl heteroaryl, and phenyl are optionally substituted with one or two substituents each independently selected from C$_{1-6}$alkyl, C$_{1-6}$alkoxy, halogen, hydroxy or C$_{1-6}$perfluoroalkyl or C$_{1-6}$perfluoroalkoxy;

n is an integer 2-5;

X$_1$ is hydrogen or C$_{1-6}$alkyl; and

X$_1$ is hydrogen or C$_{1-6}$alkyl; and

X$_2$, is selected from the group consisting of hydrogen and halogen;

X$_3$ and X$_4$ are selected from the group consisting of hydrogen, hydroxy, halogen, C$_1$-C$_6$alkoxy C$_1$-C$_6$alkyl and C$_1$-C$_6$perfluoralkyl; and X$_5$ is hydrogen with the proviso that (a) when A is O, n is 2 and X$_1$ X$_2$, X$_3$, X$_4$ and X$_5$ are hydrogen, both R$_1$ and R$_2$ are other than methyl or ethyl simultaneously;

(b) when A is O, n is 2 and X$_1$ X$_2$, X$_3$, X$_4$ and X$_5$ are hydrogen, R$_1$ and R$_2$ are other than hydrogen simultaneously;

(c) when A is O, n is 2, R$_1$ and R$_2$ are ethyl and X$_1$ X$_2$, X$_4$ and X$_5$ are hydrogen X$_3$ is other than methyl;

(d) when A is O, n is 2, R$_1$ and R$_2$ are ethyl and X$_1$ X$_2$, X$_3$ and X$_5$ are hydrogen, X$_4$ is other than methyl;

(e) when A is O, n is 2, R$_1$ and R$_2$ are ethyl and X$_1$ X$_2$, X$_3$ and X$_4$ are hydrogen, X$_5$ is other than methyl;

(f) when A is O, n is 2, R$_1$ and R$_2$ are ethyl and X$_1$ X$_2$, X$_4$ and X$_5$ are hydrogen X$_3$ is other than bromo;

(g) when A is O, n is 2, X$_1$, X$_3$ and X$_4$ are hydrogen and X$_2$, X$_5$ are methyl, R$_1$ and R$_2$ are other than hydrogen simultaneously;

(h) when A is O and n is 3 to 5, X$_1$, X$_3$, X$_4$ are hydrogen and X$_2$ and X$_5$ are both methyl, R$_1$ and R$_2$ are other than ethyl simultaneously;

or the pharmaceutically acceptable salts and optical isomers thereof.

The present invention is also directed to pharmaceutical compositions of formula (I).

Additionally the present invention is directed to methods of using the compound of formula (1) and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase.

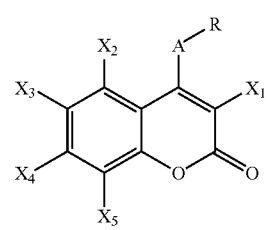

wherein:

A is O or a bond;

when A is O, R is selected from the group consisting of C$_{1-6}$alkylsulfonyl, cyanoC$_1$-C$_6$alkyl, carboxyC$_1$-C$_6$alkyl, hydroxy C$_1$-C$_6$alkyl, C$_1$-C$_6$alkoxycarbonylC$_{3-8}$cycloalkylC$_1$-C$_6$alkyl, carboxyC$_{3-8}$cycloalkylC$_1$-C$_6$alky, arylC$_1$-C$_6$alkyl, heteroarylC$_1$-C$_6$alkyl, heterocyclyl, heterocyclylC$_1$-C$_6$alkyl, heterocyclyloxyC$_1$-C$_6$alkyl, heteroarylsulfonyl, wherein aryl heteroaryl and heterocyclyl are optionally substituted with one or two substituents each independently selected from C$_{1-6}$alkyl, C$_{1-6}$alkoxy, halogen, hydroxy or C$_{1-6}$perfluoroalkyl or C$_{1-6}$perfluoroalkoxy and (CH$_2$)$_n$NR$_1$R$_2$,wherein R$_1$ R$_2$ are the same or different and are selected from, the group consisting of hydrogen, C$_1$-C$_6$ alkyl, C$_{2-6}$alkenyl, C$_{2-6}$alkynyl, C$_{1-6}$perfluoroalkyl, C$_{3-8}$cycloalkyl, C$_{3-8}$cycloalkylC$_{1-6}$alkyl, C$_{1-6}$alkoxyC$_{1-6}$alkyl, hydroxyC$_{1-6}$alkyl, aminoC$_{1-6}$alkyl, mono- or di-C$_{1-6}$-alkyl-aminoC$_{1-6}$alkyl, formyl, C$_{3-6}$alkylcarbonyl, aminoC$_{1-6}$alkylcarbonyl, C$_{1-6}$alkoxycarbonyl, I, C$_{1-6}$alkysulfonyl, C$_{1-6}$alkylaminothiocarbonyl aryl, diphenylC$_{1-6}$alkyl and arylC$_{1-6}$alkyl, arylcarbonylC$_{1-6}$ alkyl, aryloxyC$_{1-6}$alkyl, C($=$NH)NH$_2$; COOR$_3$ and, wherein R$_3$ is C$_1$-C$_6$ alkyl, wherein aryl is optionally substituted with one or two substituents each independently selected from C$_{1-6}$alkyl, C$_{1-6}$alkoxy, halogen, hydroxy or C$_{1-6}$perfluoroalkyl or C$_{1-6}$perfluoroalkoxy;

when A is a bond, R is selected from the group consisting of carboxy C$_1$-C$_6$alkyl, aminocarbonylC$_1$-C$_6$alkyl, cyanoC$_1$-C$_6$alkyl (CH$_2$)$_n$NHR$_1$, wherein R$_1$ is selected from, the group consisting of hydrogen, C$_1$-C$_6$alkyl, C$_{2-6}$alkenyl, C$_{2-6}$alkynyl, C$_{1-6}$perfluoroalkyl, C$_{3-8}$cycloalkyl, C$_{3-8}$cycloalkylC$_{1-6}$alkyl, C$_{1-6}$alkoxyC$_{1-6}$alkyl, hydroxyC$_{1-6}$alkyl, aminoC$_{1-6}$alkyl, mono- or di-C$_{1-6}$alkyl-aminoC$_{1-6}$alkyl, formyl, C$_{1-6}$alkylcarbonyl, aminoC$_{1-6}$alkylcarbonyl, C$_{1-6}$alkoxycarbonyl, C$_{1-6}$alkysulfonyl, C$_{1-6}$alkylaminothiocarbonyl, aryl, diphenylC$_{1-6}$alkyl and arylC$_{1-6}$alkyl, arylcarbonylC$_{1-6}$alkyl, heteroarylcarbonyl, aryloxyC$_{1-6}$alkyl, C($=$NH)NH$_2$ and COOR$_3$, wherein R$_3$ is C$_1$-C$_6$ alkyl, wherein aryl heteroaryl, and phenyl are optionally substituted with one or two substituents each independently selected from C$_{1-6}$alkyl, C$_{1-6}$alkoxy, halogen, hydroxy or C$_{1-6}$perfluoroalkyl or C$_{1-6}$perfluoroalkoxy;

n is an integer 2-5;

X$_1$ is hydrogen or C$_{1-6}$alkyl; and

X$_2$, X$_3$, X$_4$ and X$_5$ are the same or different and are independently selected from the group consisting of hydrogen, halogen, nitro, amino, hydroxy, C$_{1-6}$alkyl, C$_{2-6}$alkenyl, C$_{2-6}$alkynyl, C$_{1-6}$alkoxy, C$_{1-6}$perfluoroalkyl, C$_{1-6}$perfluoroalkoxy, aryl and benzyl, wherein aryl or benzyl is optionally substituted with one or two substituents each independently selected from $C_{1-6}$alkyl, $C_{1-6}$perfluoroalkyl, halogen, hydroxy or $C_{1-6}$perfluoroalkoxy or $C_{1-4}$perfluoroalkoxy;

or the pharmaceutically acceptable salts and optical isomers thereof.

It is also another object of the present invention to lower nitric oxide levels in a subject in need of such lowering. The present compounds possess useful nitric oxide synthase inhibiting activity, and are expected to be useful in the treatment or prophylaxis of a disease or condition in which the synthesis or over-synthesis of nitric oxide forms a contributory part, by administering to the patient a therapeutically effective amount of the compound of formula (I).

DETAILED DESCRIPTION OF THE INVENTION

The terms as used herein have the following meanings:

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$alkoxy", "$C_{1-6}$alkoxyC$_{1-6}$alkyl", "hydroxyC$_{1-6}$alkyl", "$C_{1-6}$alkylcarbonyl", "$C_{1-6}$alkoxycarbonylC$_{1-6}$alkyl", "$C_1$-alkoxycarbonyl", "aminoC$_{1-6}$ alkyl", "$C_{1-6}$alkylcarbamoylC$_{1-6}$alkyl", "$C_{1-6}$dialkylcarbamoylC$_{1-6}$alkyl" "mono- or di-C$_{1-6}$alkylaminoC$_{1-6}$alkyl", aminoC$_{1-6}$alkylcarbonyl", "diphenylC$_{1-6}$alkyl", "arylC$_{1-6}$alkyl", "arylcarbonylC$_{1-6}$alkyl" and "aryloxyC$_{1-6}$alkyl" are to be construed accordingly.

As used herein, the expression "$C_{2-6}$alkenyl" includes ethenyl and straight-chained or branched propenyl, butenyl, pentenyl and hexenyl groups. Similarly, the expression "$C_{2-6}$alkynyl" includes ethynyl and propynyl, and straight-chained or branched butynyl, pentynyl and hexynyl groups.

As used herein "aryl" represents a carbocyclic aromatic ring system such as phenyl, biphenyl, naphthyl, anthracenyl, phenanthrenyl, fluorenyl, indenyl, pentalenyl, azulenyl, biphenylenyl and the like. Aryl is also intended to include the partially hydrogenated derivatives of the carbocyclic aromatic systems enumerated above. Non-limiting examples of such partially hydrogenated derivatives are 1,2,3,4-tetrahydronaphthyl, 1,4-dihydronaphthyl and the like.

As used herein "aryloxy" represents a group —O-aryl wherein aryl is as defined above.

As used herein "heteroaryl" (on its own or in any combination, such as "heteroaryloxy", or "heteroaryl alkyl")—a 5-10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, tetrazole, triazole, imidazole, or benzimidazole.

As used herein "heterocyclic or heterocyclyl" (on its own or in any combination, such as "heterocyclylalkyl")—a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydro pyran, or imidazolidine.

As used herein, the expression "$C_{1-6}$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$C_{1-6}$ perfluoroalkoxy", is to be construed accordingly.

As used herein, the expression "$C_{3-8}$cycloalkyl" means cyclopropyl, cyclobutyl, cyclopentyl, cyclohexyl, cycloheptyl and cyclooctyl.

As used herein, the expression "$C_{3-8}$cycloalkylC$_{1-6}$alkyl" means that the $C_{3-8}$cycloalkyl as defined herein is further attached to $C_{1-6}$alkyl as defined herein. Representative examples include cyclopropylmethyl, 1-cyclobutylethyl, 2-cyclopentylpropyl, cyclohexylmethyl, 2-cycloheptylethyl and 2-cyclooctylbutyl and the like.

As used herein "halogen" or "halo" means chloro, fluoro, bromo, and iodo.

As used herein "$C_{1-6}$alkylsulfonyl" in the present context designates a group —S(=O)$_2$C$_{1-6}$alkyl wherein C$_{1-6}$alkyl is as defined above. Representative examples include, but are not limited to, methylsulfonyl, ethylsulfonyl, n-propylsulfonyl, isopropylsulfonyl, butylsu lfonyl, iso-butylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl and the like.

As used herein "arylsulfonyl" represents a group —S(=O)$_2$ aryl wherein aryl is as defined above.

As used herein "heteroarylsulfonyl" represents a group —S(=O)$_2$heteroaryl wherein heteroaryl is as defined above.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is a pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist either as hydrated or can be substantially anhydrous. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). It is to be understood that all such isomers and mixtures thereof in any proportion are encompassed within the scope of the present invention.

"Substituted" means substituted by 1 to 2 substituents independently selected from the group consisting of $C_{1-6}$ alkyl, $C_{1-6}$ perfluoroalkyl, hydroxy, —$CO_2H$, an ester, an amide, $C_1$-$C_6$ alkoxy, $C_1$-$C_6$ perfluoroalkoxy,—$NH_2$, Cl, Br, I, F, —NH-lower alkyl, and —N(lower alkyl)$_2$.

"Therapeutically effective amount" means an amount of the compound which is effective in treating the named disorder or condition.

As used in the examples and preparations that follow, the terms used therein shall have the meanings indicated: "kg" refers to kilograms, "g" refers to grams, "mg" refers to milligrams, "μg" refers to micrograms, "μg" refers to picograms, "mol" refers to moles, "mmol" refers to millimoles, "nmole" refers to nanomoles, "L" refers to liters, "mL" or "ml" refers to milliliters, "μL" refers to microliters, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "$[a]^{20}_D$" refers to specific rotation of the D line of sodium at 20° C. obtained in a 1 decimeter cell, "c" refers to concentration in g/mL, "THF" refers to tetrahydrofuran, "DMF" refers to dimethylformamide, "NMP" refers to 1-methyl-2-pyrrolidinone, "brine" refers to a saturated aqueous sodium chloride solution, "M" refers to molar, "mM" refers to millimolar, "μM" refers to micromolar, "nM" refers to nanomolar, "TLC" refers to thin layer chromatography, "HPLC" refers to high performance liquid chromatography, "HRMS" refers to high resolution mass spectrum, "CIMS" refers to chemical ionization mass spectrometry, "$t_R$" refers to retention time, "lb" refers to pounds, "gal" refers to gallons, "L.O.D." refers to loss on drying, "μCi" refers to microcuries, "i.p." refers to intraperitoneally, "i.v." refers to intravenously.

In one aspect of this invention there is disclosed compounds of the formula (I):

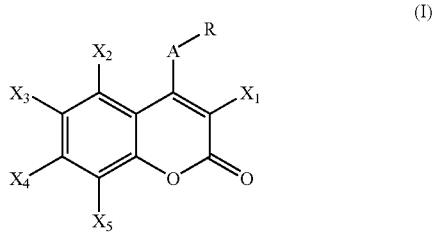

(I)

wherein:
A is O or a bond;
when A is O, R is selected from the group consisting of $C_{1-6}$alkylsulfonyl, cyano$C_1$-$C_6$alkyl, carboxy$C_1$-$C_6$alkyl, hydroxy $C_1$-$C_6$alkyl, $C_1$-$C_6$alkoxycarbonyl$C_3$-$C_8$cycloalkyl$C_1$-$C_6$alkyl, carboxy$C_3$-$C_8$cycloalkyl$C_1$-$C_6$alky, aryl$C_1$-$C_6$alkyl, heteroaryl$C_1$-$C_6$alkyl, heterocyclyl, heterocyclyl$C_1$-$C_6$alkyl, heterocyclyloxy$C_1$-$C_6$alkyl, heteroarylsulfonyl, wherein aryl heteroaryl and heterocyclyl are optionally substituted with one or two substituents each independently selected from $C_{1-6}$alkyl, $C_{1-6}$alkoxy, halogen, hydroxy or $C_{1-6}$perfluoroalkyl or $C_{1-6}$perfluoroalkoxy and $(CH_2)_nNR_1R_2$,wherein $R_1$, $R_2$ are the same or different and are selected from, the group consisting of hydrogen, $C_1$-$C_6$ alkyl, $C_{2-6}$alkenyl, $C_{2-6}$alkynyl, $C_{1-6}$perfluoroalkyl, $C_{3-8}$cycloalkyl, $C_{3-8}$cycloalkyl$C_{1-6}$alkyl, $C_{1-6}$alkoxy$C_{1-6}$alkyl, hydroxy$C_{1-6}$alkyl, amino$C_{1-6}$alkyl, mono- or di-$C_{1-6}$alkyl-amino$C_{1-6}$alkyl, formyl, $C_{3-6}$alkylcarbonyl, amino$C_{1-6}$alkylcarbonyl, $C_{1-6}$alkoxycarbonyl, I, $C_{1-6}$alkylsulfonyl, $C_{1-6}$alkylaminothiocarbonyl aryl, diphenyl$C_{1-6}$alkyl and aryl$C_{1-6}$alkyl, arylcarbonyl$C_{1-6}$ alkyl, aryloxy$C_{1-6}$alkyl, $CNHNH_2$; $COOR_3$ and, wherein $R_3$ is $C_1$-$C_6$ alkyl, wherein aryl is optionally substituted with one or two substituents each independently selected from $C_{1-6}$alkyl, $C_{1-6}$alkoxy, halogen, hydroxy or $C_{1-6}$perfluoroalkyl or $C_{1-6}$perfluoroalkoxy;

when A is a bond, R is selected from the group consisting of carboxy $C_1$-$C_6$alkyl, aminocarbonyl$C_1$-$C_6$alkyl, cyano$C_1$-$C_6$alkyl $(CH_2)_nNHR_1$, wherein $R_1$ is selected from, the group consisting of hydrogen, $C_1$-$C_6$alkyl, $C_{2-6}$alkenyl, $C_{2-6}$alkynyl, $C_{1-6}$perfluoroalkyl, $C_{3-8}$cycloalkyl, $C_{3-8}$cycloalkyl$C_{1-6}$alkyl, $C_{1-6}$alkoxy$C_{1-6}$alkyl, hydroxy$C_{1-6}$alkyl, amino$C_{1-6}$ alkyl, mono- or di-$C_{1-6}$alkyl-amino$C_{1-6}$alkyl, formyl, $C_{1-6}$alkylcarbonyl, amino$C_{1-6}$alkylcarbonyl, $C_{1-6}$alkoxycarbonyl, $C_{1-6}$alkylsulfonyl, $C_{1-6}$alkylaminothiocarbonyl, aryl, diphenyl$C_{1-6}$alkyl and aryl$C_{1-6}$ alkyl, arylcarbonyl$C_{1-6}$alkyl, heteroarylcarbonyl, aryloxy$C_{1-6}$alkyl, $C(=NH)NH_2$ and $COOR_3$, wherein $R_3$ is $C_1$-$C_6$ alkyl, wherein aryl heteroaryl, and phenyl are optionally substituted with one or two substituents each independently selected from $C_{1-6}$alkyl, $C_{1-6}$alkoxy, halogen, hydroxy or $C_{1-6}$perfluoroalkyl or $C_{1-6}$perfluoroalkoxy;

n is an integer 2-5;
$X_1$ is hydrogen or $C_{1-6}$alkyl; and
$X_2$, is selected from the group consisting of hydrogen and halogen;
$X_3$ and $X_4$ are selected from the group consisting of hydrogen, hydroxy, halogen, $C_1$-$C_6$alkoxy $C_1$-$C_6$alkyl and $C_1$-$C_6$perfluoralkyl; and
$X_5$ is hydrogen with the proviso that
(a) when A is O, n is 2 and $X_1$ $X_2$, $X_3$, $X_4$ and $X_5$ are hydrogen, both $R_1$ and $R_2$ are other than methyl or ethyl simultaneously;
(b) when A is O, n is 2 and $X_1$ $X_2$, $X_3$, $X_4$ and $X_5$ are hydrogen, $R_1$ and $R_2$ are other than hydrogen simultaneously;
(c) when A is O, n is 2, $R_1$ and $R_2$ are ethyl and $X_1$ $X_2$, $X_4$ and $X_5$ are hydrogen $X_3$ is other than methyl;
(d) when A is O, n is 2, $R_1$ and $R_2$ are ethyl and $X_1$ $X_2$, $X_3$ and $X_5$ are hydrogen, $X_4$ is other than methyl;
(e) when A is O, n is 2, $R_1$ and $R_2$ are ethyl and $X_1$ $X_2$, $X_3$ and $X_4$ are hydrogen, $X_5$ is other than methyl;
(f) when A is O, n is 2, $R_1$ and $R_2$ are ethyl and $X_1$ $X_2$, $X_4$ and $X_5$ are hydrogen $X_3$ is other than bromo;
(g) when A is O, n is 2, $X_1$, $X_3$ and $X_4$ are hydrogen and $X_2$, $X_5$ are methyl, $R_1$ and $R_2$ are other than hydrogen simultaneously;
(h) when A is O and n is 3 to 5, $X_1$, $X_3$, $X_4$ are hydrogen and $X_2$ and $X_5$ are both methyl, $R_1$ and $R_2$ are other than ethyl simultaneously;

or the pharmaceutically acceptable salts and optical isomers thereof.

Specific compounds that are part of this embodiment without limitation include:
6-Chloro-4-(3-aminopropoxy)-1-benzopyran-2-one,
4-(3-Dimethylamino-propoxy)-1-benzopyran-2-one,
6-Chloro-4-(3-methylamino-propoxy)-1-benzopyran-2-one,
4-(2-Amino-ethoxy)-1-benzopyran-2-one,
4-(2-Amino-ethoxy)-6-chloro-1-benzopyran-2-one,
4-(2-Methylamino-ethoxy)-1-benzopyran-2-one,
N-[2-(2-Oxo-2H-1-benzopyran-4-yloxy)-ethyl]-acetamide,
N-[2-(2-Oxo-2 H-1-benzopyran-4-yloxy)-ethyl]-guanidine,
4-(3-Amino-propoxy)-6,7-dimethyl-1-benzopyran-2-one,
4-(3-Amino-propoxy)-7-methoxy-1-benzopyran-2-one,
4-(3-Amino-propoxy)-6-bromo-1-benzopyran-2-one,
4-(3-Amino-propoxy)-6-fluoro-1-benzopyran-2-one,
4-(3-Amino-propoxy)-6-methoxy-1-benzopyran-2-one,
4-(3-Amino-propoxy)-6-methyl-1-benzopyran-2-one,
4-(3-Amino-propoxy)-6,8-dibromo-1-benzopyran-2-one,
[3-(5-Chloro-2-oxo-2H-1-benzopyran-4-yloxy)-propyl]-carbamic acid tert-butyl ester,
4-(3-Amino-propoxy)-5-chloro-1-benzopyran-2-one,
4-(3-Amino-propoxy)-1-benzopyran-2-one,
4-(3-Methylamino-propoxy)-1-benzopyran-2-one,
4-(3-Dimethylamino-propoxy)-7-methoxy-1-benzopyran-2-one,
6-Chloro-4-(3-dimethylamino-propoxy)-1-benzopyran-2-one,
4-(3-Dimethylamino-propoxy)-6-methyl-1-benzopyran-2-
4-(3-Dimethylamino-propoxy)-6,7-dimethyl-1-benzopyran-2-one,
N-[3-(2-Oxo-2H-1-benzopyran-4-yloxy)-propyl]-guanidine,
1-[3-(6-Chloro-2-oxo-2H-1-benzopyran-4-yloxy)-propyl]-3-methyl-thiourea,
1-Methyl-3-[3-(2-oxo-2H-1-benzopyran-4-yloxy)-propyl]-thiourea),
N-[3-(6-Chloro-2-oxo-2H-1-benzopyran-4-yloxy)-propyl]-guanidine,
N-[3-(6-Chloro-2-oxo-2H-1-benzopyran-4-yloxy)-propyl]-acetamide,
4-(4-Amino-butoxy)-5-chloro-1-benzopyran-2-one,
4-(4-Amino-butoxy)-6-chloro-1-benzopyran-2-one,
4-(5-Amino-pentyloxy)-6-chloro-1-benzopyran-2-one,
6-Chloro-4-(piperidin-3-ylmethoxy)-1-benzopyran-2-one,
6-Chloro-4-(2-piperidin-2-yl-ethoxy)-1-benzopyran-2-one,
6-Bromo-4-(piperidin-4-yloxy)-1-benzopyran-2-one,
6-Chloro-4-(pyridin-2-ylmethoxy)-1-benzopyran-2-one,
6-Chloro-4-(pyridin-3-ylmethoxy)-1-benzopyran-2-one,
6-Chloro-4-(pyridin-4-ylmethoxy)-1-benzopyran-2-one,
4-(3-Amino-propoxy)-6-chloro-3-methyl-1-benzopyran-2-one
4-(3-Amino-benzyloxy)-6-chloro-1-benzopyran-2-one,
N-[3-(6-Chloro-2-oxo-2H-1-benzopyran-4-yloxy)-propyl]-isonicotinamide,
N-[3-(6-Chloro-2-oxo-2H-1-benzopyran-4-yloxy)-propyl]-nicotinamide,
6-Methyl4-((R)-1-pyrrolidin-2-ylmethoxy)-1-benzopyran-2-one,
6-Methyl-4-((S)-1-pyrrolidin-2-ylmethoxy)-1-benzopyran-2-one,
N-[3-(6-Chloro-2-oxo-2H-1-benzopyran-4-yloxy)-propyl]-methanesulfonamide,
Butane-1-sulfonic acid 6-chloro-2-oxo-2H-1-benzopyran-4-yl ester,
5-Bromo-thiophene-2-sulfonic acid 6-chloro-2-oxo-2H-1-benzopyran-4-yl ester,
6-Bromo-4-[3-(tetrahydro-pyran-2-yloxy)-propoxy]-1-benzopyran-2-one,
6-Bromo-4-(3-hydroxy-propoxy)-1-benzopyran-2-one,
4-But-3-enyloxy-1-benzopyran-2-one,
trans-2-(6-Chloro-2-oxo-2H-1-benzopyran-4-yloxymethyl)-cyclopropanecarboxylic acid methyl ester,
trans-2-(6-Chloro-2-oxo-2H-1-benzopyran-4-yloxymethyl)-cyclopropanecarboxylic acid,
4-(6-Chloro-2-oxo-2H-1-benzopyran-4-yl)-butyronitrile,
4-(4-Aminobutyl)-6-chloro-1-benzopyran-2-one,
4-(6-Chloro-2-oxo-2H-1-benzopyran-4-yl)-pentanenitrile,
4-(5-Amino-pentyl)-6-chloro-1-benzopyran-2-one,
4-(6-Chloro-2-oxo-2H-1-benzopyran-4-yloxy)-butyramide,
4-(5-Amino-pentyl)-6-chloro-1-benzopyran-2-one, and
2-[3-(2-Oxo-2H-1-benzopyran-4-yloxy)-propyl]-isoindole-1,3-dione.

A further aspect of this embodiment relates to compounds in which A is O, R is $(CH_2)_nNR_1R_2$, $C_{1-6}$alkysulfonyl or heteroarylsulfonyl, $X_2$ is hydrogen, $X_3$ is hydrogen, halogen; $C_1$-$C_6$alkoxy or $C_1$-$C_6$alkyl, and $X_4$ is hydrogen, $C_1$-$C_6$alkoxy or $C_1$-$C_6$alkyl.

In a further embodiment of this invention compounds wherein A is O, R is $(CH_2)_nNR_1R_2$, $X_2$ is hydrogen, $X_3$ is hydrogen, halogen; $C_1$-$C_6$alkoxy or $C_1$-$C_6$alkyl, and $X_4$ is hydrogen, $C_1$-$C_6$alkoxy or $C_1$-$C_6$alkyl are disclosed.

In a further aspect of this embodiment of this invention compounds in which $R_1R_2$ are selected from the group consisting of hydrogen, $C_1$-$C_6$alkyl and $CNHNH_2$ are described.

In a further aspect of this embodiment, compounds wherein $X_3$ is halogen selected from the group consisting of bromine, chlorine and fluorine and $X_4$ is hydrogen are disclosed.

In another embodiment of this invention, compounds are disclosed wherein $X_3$ is chlorine.

In another embodiment of this invention, compounds of formula (I) wherein A is a bond, R is $(CH_2)NHR_1$, or aminocarbonyl$C_1$-$C_6$alkyl are disclosed.

In a further aspect of this embodiment, $R_1$ is hydrogen.

In a further embodiment of this invention, the compounds wherein $X_3$ is a halogen and $X_4$, $X_5$ and $X_6$ are hydrogen are disclosed.

In another embodiment of this invention, compounds wherein $X_3$ is chlorine are disclosed.

In another aspect of this invention, there is disclosed a method of treating a disease, which is characterized by production of nitric oxide by the inducible form of nitric oxide synthase and wherein the selected compound inhibits said production of nitric oxide, which comprises administering to said mammal having said disease a therapeutically effective amount of a compound of the formula (I):

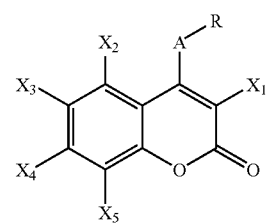

wherein:
A is O or a bond;
when A is O, R is selected from the group consisting of $C_{1-6}$alkylsulfonyl, cyano$C_1$-$C_6$alkyl, carboxy$C_1$-

$C_6$alkyl, hydroxy $C_1$-$C_6$alkyl, $C_1$-$C_6$alkoxycarbonylC$_3$-$C_8$cycloalkylC$_1$-$C_6$alky, carboxyC$_3$-$C_8$cycloalkylC$_1$-$C_6$alky, arylC$_1$-$C_6$alkyl, heteroarylC$_1$-$C_6$alkyl, heterocyclyl, heterocyclylC$_1$-$C_6$alkyl, heterocyclyloxyC$_1$-$C_6$alkyl, heteroarylsulfonyl, wherein aryl heteroaryl and heterocyclyl are optionally substituted with one or two substituents each independently selected from $C_{1-6}$alkyl, $C_{1-6}$alkoxy, halogen, hydroxy or $C_{1-6}$perfluoroalkyl or $C_{1-6}$perfluoroalkoxy and $(CH_2)_n NR_1R_2$, wherein $R_1$ $R_2$ are the same or different and are selected from, the group consisting of hydrogen, $C_1$-$C_6$ alkyl, $C_{2-6}$alkenyl, $C_{2-6}$alkynyl, $C_{1-6}$perfluoroalkyl, $C_{3-8}$cycloalkyl, $C_{3-8}$cycloalkylC$_{1-6}$alkyl, $C_{1-6}$alkoxyC$_{1-6}$alkyl, hydroxyC$_{1-6}$alkyl, aminoC$_{1-6}$alkyl, mono- or di-$C_{1-6}$alkyl-aminoC$_{1-6}$alkyl, formyl, $C_{3-6}$alkylcarbonyl, aminoC$_{1-6}$alkylcarbonyl, $C_{1-6}$alkoxycarbonyl, I, $C_{1-6}$alkysulfonyl, $C_{1-6}$alkylaminothiocarbonyl aryl, diphenylC$_{1-6}$alkyl and arylC$_{1-6}$alkyl, arylcarbonylC$_{1-6}$ alkyl, aryloxyC$_{1-6}$alkyl, C(=NH)NH$_2$; COOR$_3$ and, wherein R$_3$ is $C_1$-$C_6$ alkyl, wherein aryl is optionally substituted with one or two substituents each independently selected from $C_{1-6}$alkyl, $C_{1-6}$alkoxy, halogen, hydroxy or $C_{1-6}$perfluoroalkyl or $C_{1-6}$perfluoroalkoxy;

when A is a bond, R is selected from the group consisting of carboxy $C_1$-$C_6$alkyl, aminocarbonylC$_1$-$C_6$alkyl, cyanoC$_1$-$C_6$alkyl $(CH_2)_n NHR_1$, wherein $R_1$ is selected from, the group consisting of hydrogen, $C_1$-$C_6$alkyl, $C_{2-6}$alkenyl, $C_{2-6}$alkynyl, $C_{1-6}$perfluoroalkyl, $C_{3-8}$cycloalkyl, $C_{3-8}$cycloalkylC$_{1-6}$alkyl, $C_{1-6}$alkoxyC$_{1-6}$alkyl, hydroxyC$_{1-6}$alkyl, aminoC$_{1-6}$alkyl, mono- or di-$C_{1-6}$alkyl-aminoC$_{1-6}$alkyl, formyl, $C_{1-6}$alkylcarbonyl, aminoC$_{1-6}$alkylcarbonyl, $C_{1-6}$alkoxycarbonyl, $C_{1-6}$alkysulfonyl, $C_{1-6}$alkylaminothiocarbonyl, aryl, diphenylC$_{1-6}$alkyl and arylC$_{1-6}$ alkyl, arylcarbonylC$_{1-6}$alkyl, heteroarylcarbonyl, aryloxyC$_{1-6}$alkyl, CNHNH$_2$ and COOR$_3$, wherein R$_3$ is $C_1$-$C_6$ alkyl, wherein aryl heteroaryl, and phenyl are optionally substituted with one or two substituents each independently selected from $C_{1-6}$alkyl, $C_{1-6}$alkoxy, halogen, hydroxy or $C_{1-6}$perfluoroalkyl or $C_{1-6}$perfluoroalkoxy;

n is an integer 2-5;

$X_1$ is hydrogen or $C_{1-6}$alkyl; and $X_2$, $X_3$, $X_4$ and $X_5$ are the same or different and are independently selected from the group consisting of hydrogen, halogen, nitro, amino, hydroxy, $C_{1-6}$alkyl, $C_{2-6}$alkenyl, $C_{2-6}$alkynyl, $C_{1-6}$alkoxy, $C_{1-6}$perfluoroalkyl, $C_{1-6}$perfluoroalkoxy, aryl and benzyl, wherein aryl or benzyl is optionally substituted with one or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;

or the pharmaceutically acceptable salts and optical isomers thereof.

In this embodiment a specific disease or disorder that can be treated with the compound of this invention of this invention without any limitation include: multiple sclerosis, stroke or cerebral ischemia, Alzheimer's disease, HIV dementia, Parkinson's disease, meningitis, dilated cardiomyopathy and congestive heart failure, atherosclerosis, restenosis or graft stenosis, septic shock, hemorrhagic shock, asthma, adult respiratory distress syndrome, smoke or particulate-mediated lung injury, pathogen-mediated pneumonias, rheumatoid arthritis and osteoarthritis, glomerulonephritis, systemic lupus erythematosus, inflammatory bowel diseases, insulin dependent diabetes mellitus, diabetic neuropathy or nephropathy, acute and chronic organ transplant rejection, transplant vasculopathies, graft-versus-host disease, psoriasis, and cancer.

The compounds disclosed herein can be synthesized according to the following procedures of Schemes A-F, wherein the X, and R substituents are as identified for formula (I), above unless otherwise noted. If necessary, in the following synthetic schemes, reactive functional groups present in the compounds described in this invention may be protected by suitable protecting groups. The protecting group may be removed at a later stage of the synthesis. Procedures for protecting reactive functional groups and their subsequent removal may be found in T. W. Greene and P. G. M. Wuts, *Protective Groups in Organic Synthesis*, Wiley and Sons, 1991.

The synthesis of the appropriate starting materials, the 4-hydroxy coumarins, intermediates for compounds of formula 1 wherein A is O may be accomplished by methods well known in the art (see U.S. Pat. No. 5,959,109 issued Sep. 28, 1999, incorporated herein by reference). For instance, shown in Scheme A is a general synthesis of 4-hydroxycoumarins is depicted.

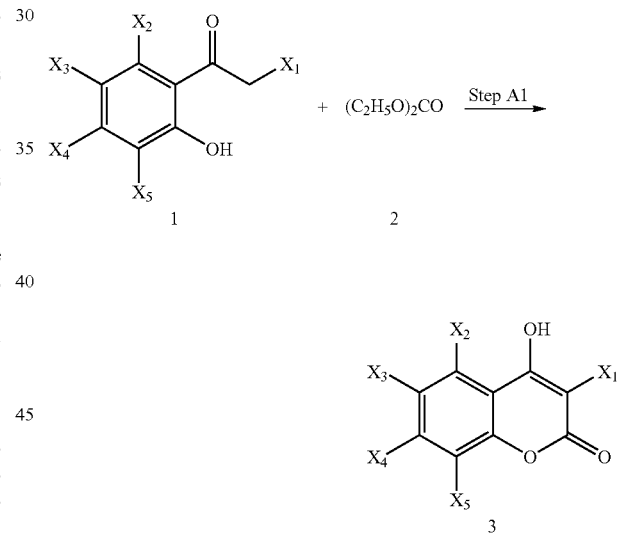

In scheme A step A1 a suitably substituted ortho-hydroxyalkylphenone 1 is reeacted with diethylcarbonate 2 to produce the desired 4-hydroxycoumarin 3. The reaction is generally carried out in an inert solvent, for instance toluene, in the presence of a base that is capable of extracting the hydrogen of the alkyl chain at the alpha position to the carbonyl function to form the anion. Suitable bases include alkali metal hydrides such as sodium hydride, lithium hydride and potassium hydride. Other strong bases such as lithium diisopropylamide, potassium amide, sodium amide or potassium t-butoxide and the like may also be used. The reaction is generally carried out at ambient temperature to the boiling point of the inert solvent.

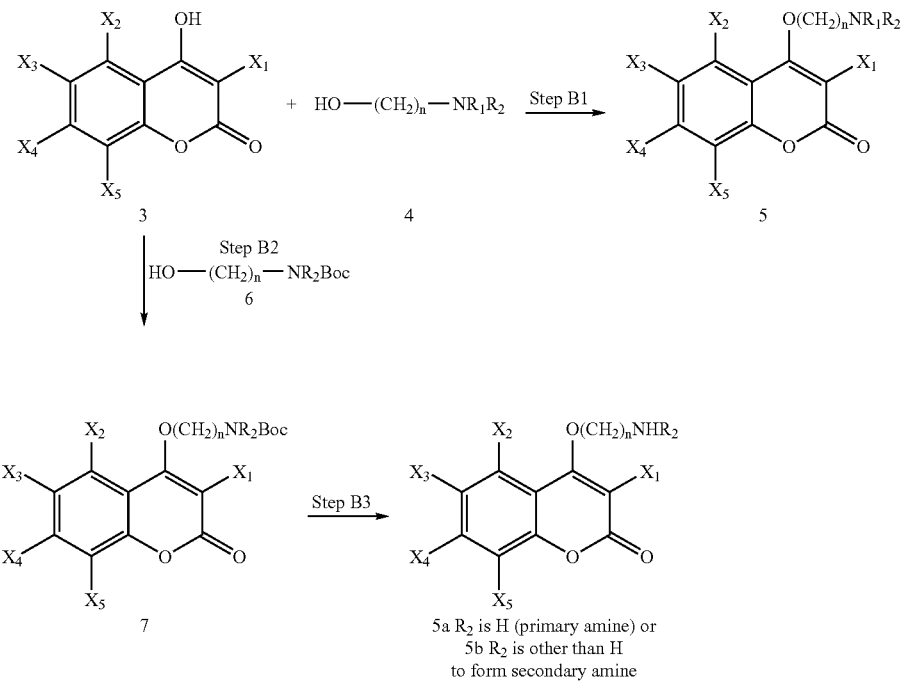

Scheme B

In Scheme B is depicted methods for the synthesis of the compounds of formula (I) that retain an oxygen moiety at the 4-position (A is O) and contain an aminoalkylmoiety ($(CH_2)_n NR_1R_2$). Accordingly, as shown in step B1 the appropriately substituted 4-hydroxy coumarin 3 is reacted under Mitsunobu conditions (see Suzuki E., et al., *J. Chem. Res. (S)*, 1979, 110, also Ito, K., et al., *Heterocycles*, 1997, 46, 567-580) with the appropriate aminoalcohol 4 in the presence of a suitable dehydrating agent in an inert solvent such as tetrahydrofuran to afford the 4-aminoalkoxycoumarin 5. Suitable dehydrating agents are triphenylphosphine, diethylazodicarboxylate, diisopropylazodicarboxylate, 1,3-dicyclohexylcarbodiimide and Amberlyst-15. The reaction is generally carried out at below ambient temperature from about −78° to 0° C.

In step B2 an alternative approach is shown to the aminoalkoxy coumarins. Compound 3 is reacted with a Boc-protected aminoalkyl compound 6, under conditions described above to give compound 7.

In step B3 the Boc group is removed by the use of methods that are known in the art. For example, reaction of compound 7 with a strong acid neat or in the presence of an inert solvent can effect the removal of Boc group to produce the primary amine 5a or the secondary amine 5b. Suitable strong acids are trifluoroacetic acid, hydrochloric acid or sulfuric acid, with trifluoroacetic acid or hydrochloric acid preferred. The reaction is typically run at sub-ambient to ambient temperatures, for example 0° to 25° C.

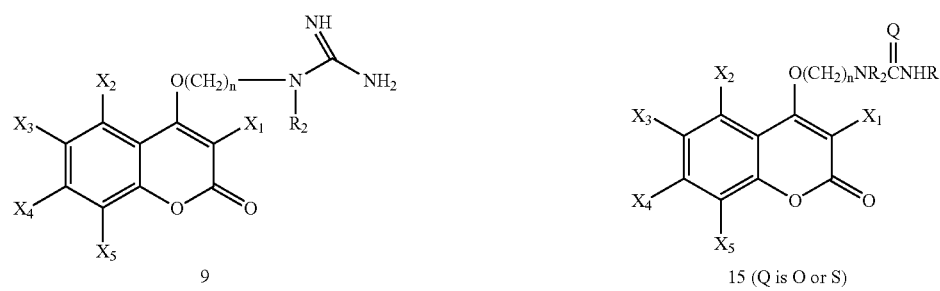

Scheme C

-continued

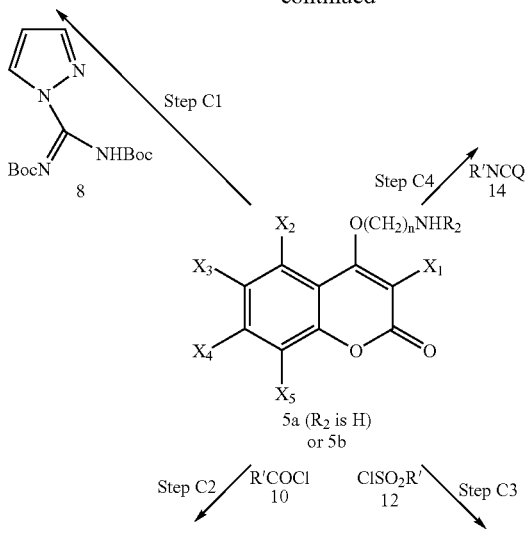

5a ($R_2$ is H)
or 5b

Scheme C illustrates methods to further elaborate the amino group of compound 5a/5b. In the Scheme, R' may be the following: alkyl, alkenyl, alkynyl, perfluoroalkyl, cycloalkyl, cycloalkylalkyl, alkoxyalkyl, mono- or di- alkylamino alkyl, alkylaryl, diphenylalkyl and arylalkyl, arylcarbonylalkyl or phenoxyalkyl. In compound 12 and 13 R' can have the additional meaning of alkylamino.

In step C1 compound 5a/b is reacted with NN'-bis(tert-butoxycarbonyl)-1H-pyrazole-1-carboxamidine, compound 8 in the presence of a suitable base and in an inert solvent such as dichloromethane, chloroform and the like to form the guanidinyl compound 9. Suitable bases include tertiary organic amines such as triethylamine, diisopropylethylamine and the like. The reaction is typically run at ambient temperature or sub-ambient temperatures, for example 0° to 25° C. See Drake, B. et al., *Synthesis*, 1994, 579-82.

In step C2 compound 5a/b can be reacted with a carboxylic acid chloride 10 or a carboxylic acid anhydride (R'CO)$_2$O utilizing methods well known in the art to produce the amide compound 11. The reaction is typically run in the presence of a suitable base to act as an acid scavenger in an inert organic solvent or solvent mixtures such as dichloromethane, DMF or DMF/dichloromethane. Suitable bases are organic amines such as triethylamine, diisopropylethylamine, pyridine or alkaline carbonates such as sodium or potassium carbonate. Diisopropylethylamine is the preferred base. The reaction is typically run at ambient temperature or sub-ambient temperatures, for example 0° to 25° C.

In step C3 the formation of the sulfonamide 13 is depicted. Accordingly, compound 5a/b is reacted with the appropriate sulfonyl chloride 12, under reaction conditions described in step C2 above.

In step C4 compound 5a/b is reacted with an isocyanate or isothiocyanate of structure 14 to produce a urea or thiourea of compound 15. The reaction is performed in an inert organic solvent or solvent mixtures such as dichloromethane, DMF or DMF/dichloromethane. The reaction is typically run at ambient temperature or sub-ambient temperatures, for example 0° to 25° C.

Scheme D

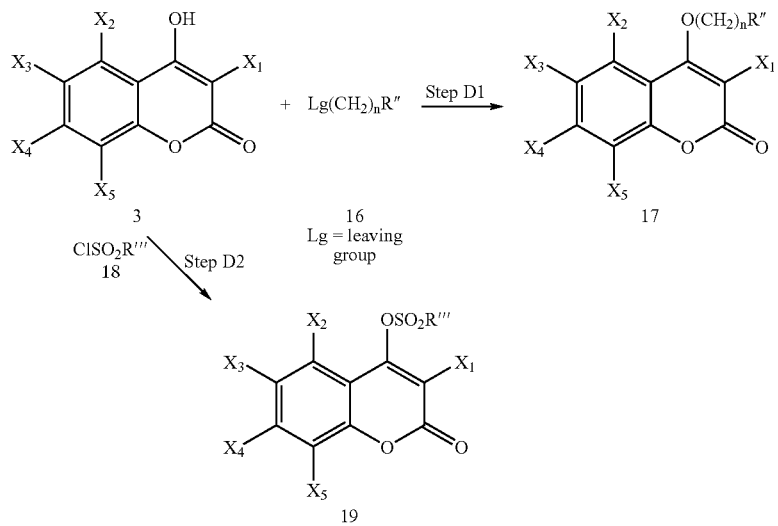

Compounds of the present invention not substituted with a terminal amino function at the 4-alkoxy substituent of the coumarin may be synthesized by the methods described in Scheme D. In the Scheme "Lg" is a leaving group for instance bromine, chlorine or iodine or sulfonate esters such as besylates, mesylates or tosylates. The R" group may be any one of the following hydrogen, cycloalkyl, cycloalkylalkyl, perfluoroalkyl, alkoxyalkyl, hydroxyalkyl, aminoalkyl, mono- or di-alkyl-aminoalkyl, formyl, alkylcarbonyl, aminoalkylcarbonyl, alkoxycarbonyl, alkoxycarbonylcycloalkylalkyl, alkylsulfonyl, alkylaminothiocarbonyl aryl, diphenylalkyl and arylalkyl, arylcarbonylalkyl, phenoxyalkyl, carboxy or $C(=NH)NH_2$. Whereas R''' may be aryl, heteroaryl, alkyl, alkenyl, alkynyl, cycloalkyl, cycloalkylalkyl, aminoalkyl, perfluoroalkyl, diphenylalkyl or arylalkyl.

In step D1 a 4-hydroxycoumarin 3 is reacted with the appropriately substituted O-alkylating agent 16 in an inert organic solvent such as DMF or acetone under basic conditions. Suitable bases are the alkaline carbonates such as sodium, potassium or cesium carbonate, with cesium carbonate preferred. The reaction is generally run at super-ambient temperatures, for example in the range of 500 to 100° C.

Synthesis of the sulfonate esters 19 is accomplished by reaction of compound 3 with the sulfonyl chloride 18, as depicted in step D2. The reaction is typically run under basic conditions in an inert organic solvent or solvent mixtures such as dichloromethane, DMF or DMF/dichloromethane. Suitable bases are tertiary organic amines such as triethylamine, diisopropylethylamine, pyridine or alkaline carbonates such as sodium or potassium carbonate. The reaction is typically run at ambient temperature or sub-ambient temperatures, for example 0° to 25° C.

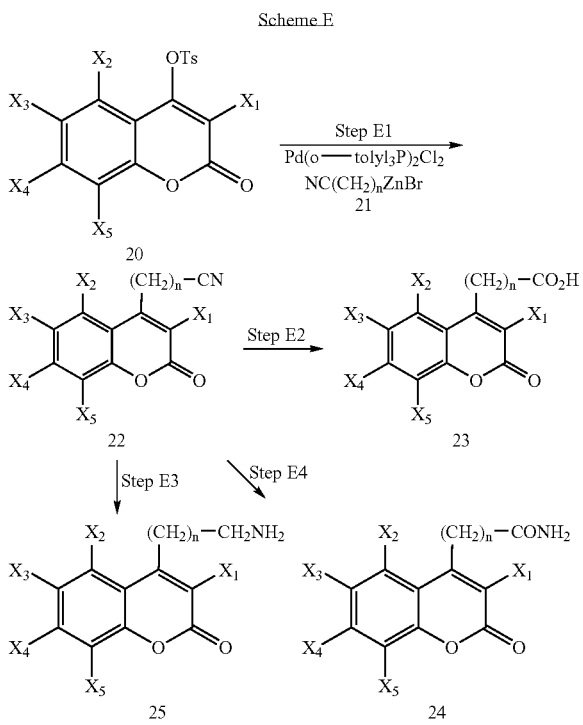

Scheme E

Scheme E illustrates the synthesis of the coumarins with a terminally substituted alkyl chain at the 4-position, the compounds of formula 1 wherein A is a bond.

In step E1 the 4-tosylated coumarin (synthesized from 3 as shown in Scheme D step D2) is reacted with a cyanoalkylzinc bromide 21 in the presence of a suitable palladium catalyst such as tritosylphosphinepalladium chloride and the like to effect a cross-coupling reaction to 4-cyanoalkyl coumarin 22. The reaction is run under an inert atmosphere such as argon or nitrogen in an inert organic solvent. Suitable solvents are acetonitrile or THF, with THF preferred. The reaction is typically run at ambient to super-ambient temperatures, for example, 250 to 60° C. The reaction has been described by Wu, J. et al., *J. Org. Chem.*, 2001, 66, 3642-3645.

As further illustrated in Scheme E compound 22 can undergo further reactions at the cyano group.

palladium on carbon, nickel aluminum oxide and Raney nickel. Raney nickel is particularly preferred. Suitable solvents are alcohols such as ethanol, propanol, isopropanol and the like. The reaction can be carried out at ambient to super-ambient temperatures, for example 250 to 70° C.

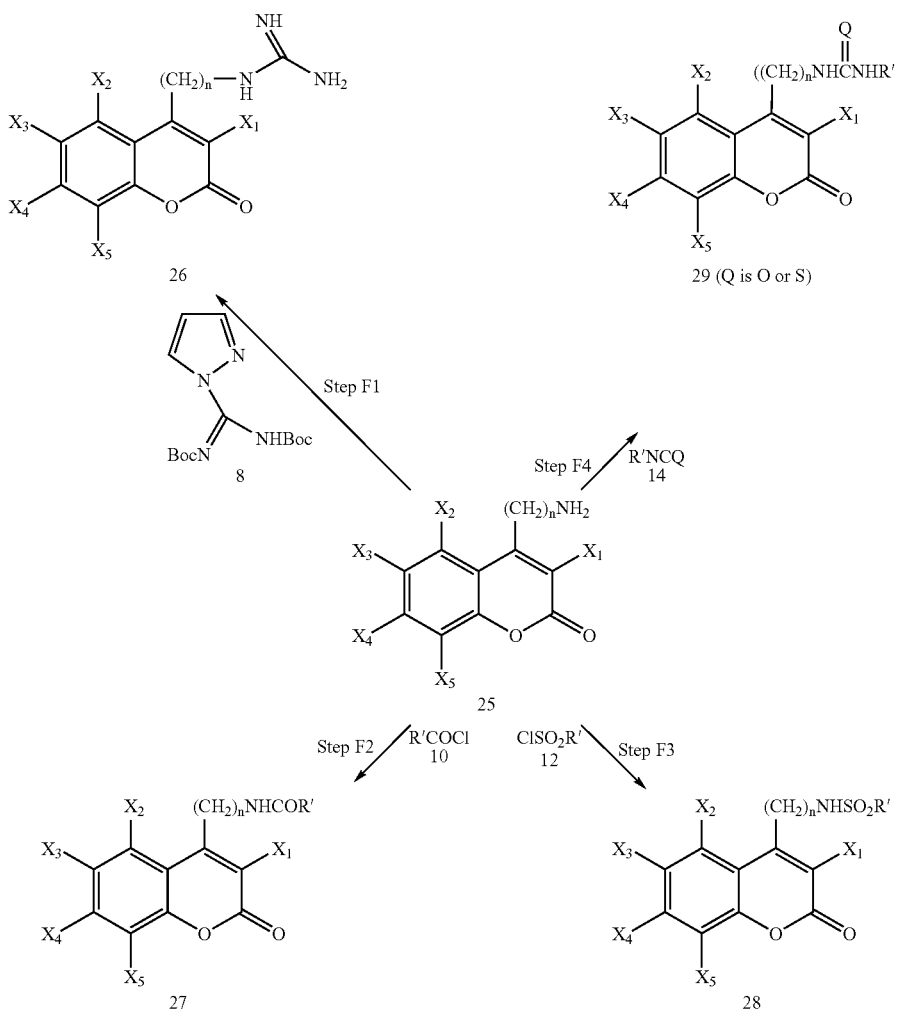

In step E2 hydrolysis of the nitrile 22 produces the carboxylic acid 23. Methods that are well known in the art can be used for instance acid or base hydrolysis (see Larock, R. C. *A Guide to Functional Group Transformations*, page 993, VCH Publishers, 1989).

In step E3 the amide 24 can be obtained from the nitrile 22 by acid or base hydrolysis. The reactions are typically run under strong acid or base conditions. Suitable acids are sulfuric, hydrochloric or polyphosphoric acid. Suitable bases are the alkali hydroxides such as sodium or potassium hydroxide. The reactions can be run with an aqueous solvent or with acids neat. Sulfuric acid neat is particularly preferred at ambient temperatures.

In step E4 the nitrile 22 is reduced to the amine derivative 25. The reduction can be readily achieved by hydrogen with a suitable catalyst in an inert solvent. Suitable catalysts are Scheme F illustrates the further transformations that may be effected upon the 4-aminoalkyl coumarin 25. In the Scheme, R' may be the following: alkyl, alkenyl, alkynyl, perfluoroalkyl, cycloalkyl, cycloalkylalkyl, alkoxyalkyl, mono- or di- alkyl-amino alkyl, alkylaryl, diphenylalkyl and arylalkyl, arylcarbonylalkyl or phenoxyalkyl. In compound 12 and 28 R' can have the additional meaning of alkylamino. In step F1 compound 25 is reacted with NN'-bis(tert-butoxycarbonyl)-1H-pyrazole-1-carboxamidine, compound 8 in the presence of a suitable base and in an inert solvent such as dichloromethane, chloroform and the like to form the guanidinyl compound 26. Suitable bases include tertiary organic amines such as triethylamine, diisopropylethylamine and the like. The reaction is typically run at ambient temperature or sub-ambient temperatures, for example 0° to 25° C.

In step F2 compound 25 can be reacted with an carboxylic acid chloride 10 or a carboxylic acid anhydride (R'CO)$_2$O utilizing methods well known in the art to produce the amide compound 27. The reaction is typically run in the presence of a suitable base to act as an acid scavenger in an inert organic solvent or solvent mixtures such as dichloromethane, DMF or DMF/dichloromethane. Suitable bases are tertiary organic amines such as triethylamine, diisopropylethylamine, pyridine or alkaline carbonates such as sodium or potassium carbonate. Diisopropylethylamine is the preferred base. The reaction is typically run at ambient temperature or sub-ambient temperatures, for example 0° to 25° C.

In step F3 the formation of the sulfonamide 28 is depicted. Accordingly, compound 25 is reacted with the appropriate sulfonyl chloride 12, under reaction conditions described for step F2 above.

In step F4 compound 25 is reacted with an isocyanate or isothiocyanate of structure 14 to produce a urea or thiourea of compound 29. The reaction is performed in an inert organic solvent or solvent mixtures such as dichloromethane, DMF or DMF/dichloromethane. The reaction is typically run at ambient temperature or subambient temperatures, for example 0° to 25° C.

BIOLOGICAL EXAMPLES

Methods for in vitro NOS Assays

Enzyme Preparations

Rat NOS-1 (nNOS) Assay:

A recombinant rat NOS-1 (neuronal) preparation is purchased from Cayman Chemical (Catalog N° 60870). This preparation corresponds to recombinant rat NOS-1 isolated from a Baculovirus overexpression system in Sf9 cells, and represents a 100,000×supernatant. To avoid thawing/freezing cycles, this enzymatic preparation is divided into small fractions (25-100 µl) stored at −80° C. until use.

Murine NOS-2 (iNOS) Assay:

A recombinant murine NOS-2 (inducible) preparation is purchased from Cayman Chemical (Catalog N° 60864). This preparation corresponds to murine NOS-2 expressed in *E. Coli*, and represents a 100,000×supernatant. To avoid thawing/freezing cycles, this enzymatic preparation is divided into small fractions (25-100 µl) stored at −80° C. until use.

Bovine NOS-3 (eNOS) Assay:

A recombinant bovine NOS-3 (endothelial) preparation is purchased from Cayman Chemical (Catalog N° 60880. This preparation corresponds to recombinant bovine NOS-3 isolated from a Baculovirus overexpression system in Sf9 cells, and represents a 100,000×supernatant. To avoid thawing/freezing cycles, this enzymatic preparation is divided into small fractions (25-100 µl) stored at −80° C. until use.

Enzymatic Assays

Experimental conditions (protein concentration, incubation time) required for measuring NOS activity (37° C.) in screening assays are controlled for each batch of enzyme prepared or commercially obtained. NOS enzymatic assays are based on the conversion of [$^3$H]-arginine into [$^3$H]-citrulline originally described by Bredt and Snyder (1990, Proc. Natl. Acad. Sci. USA 87, 682-685).

Rat NOS-1 Assay:

0.012 Units recombinant rat nNOS is incubated in Costar polystyrene 96-well microplates 20 min at 37° C. with 2 µM L-[$^3$H]arginine, 1 mM NADPH, 15 µM 6R-tetrahydrobiopterin, 1 µM FAD, and 10 µg/ml calmodulin prepared in HEPES buffer (50 mM, pH 7.4) containing 0.1 mM DL-dithiothreitol, 1 mM EDTA and 1.25 mM CaCl$_2$ (final volume: 90 µl).

0.06 µCi/well L-[$^3$H]arginine (Amersham; ~55.0 Ci/mmol, 1 mCi/ml) is used. The background level is determined in the presence of 0.5 mM of L-N$^G$-nitro-L-arginine (L-NNA; IC$_{50}$ for rat NOS-1 activity ~0.1 µM).

The incubations are terminated by using the Beckman Multimek to transfer 60 ul of the assay solution into Millipore MAHV N45 plates, packed with 80 ul/well 500 mg of AG® 50W-X$_8$ (counterion Na$^+$) cation exchange resin and prewashed with 100 ul of HEPES buffer (100 mM, pH 5.5) containing 10 mM EGTA. After filtering under vacuum into opaque scintillation plates, approximately 220 ul of Packard Microscint-40 is added to each well using a Titertek multidrop. The plates are counted on a Packard TopCount to quantify L-[$^3$H]citrulline by liquid scintillation counting.

The recovery of L-[$^3$H]citrulline can be estimated by using L-[ureido-$^{14}$C]-citrulline (NEN; 58.8 mCi/mmol) as an external standard (4.05 nCi/0.09 ml). Specific NOS I-like activity corresponds to the L-NNA-sensitive formation of L-citrulline per minute and milligram of protein (pmol/min/unit of protein).

The Km of L-arginine has been estimated at an average of 1.6 (±0.2) µM.

Murine NOS-2 Assay:

This enzymatic assay is performed as for rat NOS-1 assay with some modifications. The incubation buffer does not contain CaCl$_2$, calmodulin and EDTA (NOS-2 enzyme is not a Ca$^{2+}$-activated). 0.024 Units of iNOS are usually incubated for 20 min at 37° C. in the presence of 10 uM L-[$^3$H]arginine (0.06 uCi/well) The background level is determined in the presence of 1 mM L-N Gmethyl-arginine (L-NMA; IC$_{50}$ for murine NOS-2 activity ~2 µM).

The Km of L-arginine has been estimated at an average of 13.6 (±2.8) µM.

Human NOS-2 Assay:

Human NOS-2 obtained from Phillipe Bertrand (Vitry, Batch DBO 1131, 4.85 mg total protein per ml). This enzymatic assay is performed as for rat NOS-1 assay with some modifications. The incubation buffer does not contain CaCl$_2$, calmodulin and EDTA (NOS-2 enzyme is not a Ca$^{2+}$-activated). Human iNOS is used as 1:30 diluted preparation, is usually incubated for 60 min at 37° C. in the presence of 2.5 µM L-[$^3$H]arginine (0.06 uCi tracer/well). The background level is determined in the presence of 1 mM L-N Gmethyl-arginine.

The Km of L-arginine has been estimated at an average of 2.38 (±1.5) µM

Bovine NOS-3 Assay:

This assay is performed as for rat NOS-1 assay with some modifications. The incubation buffer does not contain EDTA. Aliquots of commercial enzyme fraction (quantity used variable from one batch to another, but normally 0.012 Units/90 ul reaction volume) are usually incubated for 120 min in the presence of 10 µM L-[$^3$H]arginine (0.15 uCi/well). The background level is determined in the presence of 0.5 mM L-NNA (IC$_{50}$ for bovine NOS-3 activity ~0.5 µM).

The Km of L-arginine has been estimated at an average of 12.2 µM.

For all NOS assays in vitro, the inhibitory activities of screened compounds (usually tested at 10$^{-9}$-10$^{-4}$ M) are represented by their IC$_{50}$ values determined by non-linear regression analysis with Activity Base Software (Data management system from IDBS Ltd).

Table 1 illustrates the effect of compounds in NOS assays.

TABLE 1

| Example | Human iNOS, $IC_{50}$ (μM) | Mouse iNOS, $IC_{50}$ (μM) | Bovine eNOS, $IC_{50}$ (μM) | Rat nNOS, $IC_{50}$ (μM) |
|---|---|---|---|---|
| 1 | 0.094* | 0.06** | >10** | 0.56* |
| 2 | 4.0* | >10 | >10 | >10 |
| 3 | 0.11** | 0.25 | >10 | 0.53 |
| 5 | 10 | | | |
| 11 | 0.1** | 0.14 | >10 | 0.36 |
| 12 | 1.1** | 0.44 | >10 | 1.6 |
| 14 | 0.3** | 0.3 | 0 > 10 | 0.65 |
| 19 | 7.6* | 7.4** | >10 | 9.1 |
| 22 | 4.1** | 1.2 | >10 | 8.0 |
| 23 | 4.7 | 3.0 | >10 | >10 |
| 28 | 0.51** | 0.39 | >10 | 0.5 |
| 31 | 2.0** | 1.0 | >10 | >10 |
| 32 | 1.3 | | | |
| 33 | | 1.5 | | |
| 34 | 2.0** | 4.2 | >10 | 1.0 |
| 57 | 3.6 | | | |

*mean of 3 determinations;
**mean of 2 determinations.

SYNTHETIC EXAMPLES

General

Commercial reagents and solvents were used as received. $^1$H NMR spectra were recorded on a Varian MercuryPlus-300 (300 MHz) or Varian Unity Inova (400 MHz) spectrometer as indicated. Proton chemical shifts are reported in δ ppm relative to internal tetramethylsilane (0.0 ppm). MS (LC-MS) data is obtained using a Micromass LCT time of flight mass spectrometer with electrospray ionization and 5 min data aquisition time for m/z 100 to 1000. LC (LC-MS) is performed using a Hypersil C18 column (4.6×50 mm, 3.5μ) with mobile phase of 0.1% TFA in $H_2O$ (A) and 0.1% TFA in ACN (B) and a gradient of 5% to 100% B over 3 min followed by 2 min at 100% B. Alternatively, a Plafform LC-MS with electrospray source may be used with a HP1100 LC system running at 2.0 ml/min, 200 μL/min split to the ESI source with inline HP1100 DAD detection and SEDEX ELS detection. A Luna C18(2) column (30×4.6 mm 3μ) is used with a gradient of 5% to 95% B over 4.5 min with mobile phase of 0.1% formic acid in $H_2O$ and 0.1% formic acid in ACN (B). HPLC purification is performed on a Varian ProStar system using a reversed-phase C18 column with a linear gradient of ACN/ $H_2O$ containing 0.1% trifluoroacetic acid. Substituted 4-hydroxycoumarin derivatives are obtained commercially or are synthesized via methods described in the literature (see U.S. Pat. No. 5,959,109). 5-Chloro-4-hydroxycoumarin is synthesized using the procedure of Snieckus et al, *Tetrahedron Letters*, 1998, 39, 4995-4998. Non-commercial Boc-protected alcohols are prepared by reaction of the commercially available amino alcohols with di-t-butyldicarboxylate using standard methods (see Critch, D. et al., *J. Org. Chem.*, 1997, 62(17) 5982-5988). trans-2-Methanesulfonyloxymethyl-cyclopropane-carboxylic acid methyl ester is prepared as described in WO 02/66446. Toluene-4-sulfonic acid 6-chloro-2-oxo-2H-1-benzopyran-4-yl ester and toluene-4-sulfonic acid 2-oxo-2H-1-benzopyran-4-yl ester are prepared by modification of literature procedures. See for example, Schio, L. et al. *Tetrahedron Letters*, 2000, 41(10), 1543-1547. Wu, J. et al., *J. Org. Chem.*, 2001, 66, 3642-3645.

Abbreviations used: Dichloromethane (DCM), dimethylformamide (DMF) methanol (MeOH), diethylether ($Et_2O$), acetonitrile (ACN), ethyl acetate (EtOAc), ethanol (EtOH), trifluoroacetic acid (TFA), tetrahydrofuran (THF), diisopropylazodicarboxylate (DIAD), diisopropylethylamine (DIEA), triphenylphosphine ($PPh_3$), t-butyloxycarbonyl (Boc); NMR abbreviations: singlet (s), doublet (d), double doublet (dd), triplet (t), quartet (q), broad (br). "Calcd" means calculated.

4-Substituted hydroxycoumarin derivatives of the present invention may be prepared by methods A, B, or C:

Method A.

EXAMPLE 1

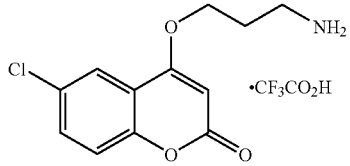

6-Chloro-4-(3-aminopropoxy)-1-benzopyran-2-one
Trifluoroacetic acid salt

6-Chloro-4-hydroxycoumarin (25.4 mmol, 5.0 g), triphenylphosphine (26.67 mmol, 6.99 g), and (3-hydroxypropyl)-carbamic acid tert-butyl ester (26.67 mmol, 4.6 mL) is suspended in 125 mL of THF. The reaction is cooled to −78° C. (smaller scale reactions <5 mmol may be run at 0° C.) and a solution of diisopropylazodicarboxylate (DIAD) (27.94 mmol, 5.48 mL) in 40 mL of THF is added dropwise via an addition funnel at −78° C. The reaction is allowed to warm slowly to ambient temperature and is stirred overnight. The reaction mixture is concentrated in vacuo and $Et_2O$ is added to precipitate a solid, which is filtered, washed with $Et_2O$, and is dried. The solid is treated with neat TFA for 30 minutes at ambient temperature. The TFA is removed under reduced pressure and $Et_2O$ is added to precipitate a white solid which is filtered, is washed with $Et_2O$, and is dried to afford the title compound as the trifluoroacetic acid salt (5.14 g). A second crop (3.1 g) could be obtained by refrigerating the filtrate overnight with an overall combined yield of 88%. $^1$H NMR (DMSO-d6, 300 MHz) δ 7.87 (1H, d, J =2.75 Hz), 7.80 (2H, br s), 7.73 (1H, dd, J=2.75, 9 Hz), 7.48 (1H, d, J=9 Hz), 5.97 (1H, s), 4.30 (2H, t, J=5.75 Hz), 3.04 (2H, br s), 2.12 (2H, m); MS (ESI, Pos.) calcd for $C_{12}H_{12}ClNO_3$ m/z [M+H]=254.1, found 254.1.

Method B.

EXAMPLE 2

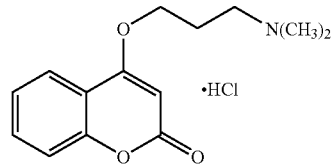

4-(3-Dimethylamino-propoxy)-1-benzopyran-2-one Hydrochloric acid salt

4-Hydroxycoumarin (3.0 mmol, 0.487 g) is dissolved in 10 mL of THF. Triphenylphosphine (3.15 mmol, 0.825 g) and 3-dimethylamino-propan-1-ol (3.15 mmol, 0.372 mL) is added and the solution is cooled to 0° C. DIAD (3.30 mmol, 0.647 g) is added dropwise at 0° C. The reaction is stirred 30 min. at 0° C then is allowed to warm to ambient temperature and is stirred overnight. The solvent is evaporated under reduced pressure, and a solution of anhydrous HCl/MeOH (prepared by adding ~5 mL acetyl chloride dropwise to 100 mL MeOH) is added to the residue. Alternatively 4M HCl in dioxane may be used. The solvent is removed under reduced pressure and the residue is treated with $Et_2O$. The resulting solid is filtered, is washed with $Et_2O$, and is dried to afford the title compound as the hydrochloric acid salt (0.485g, 57%). $^1$H NMR (DMSO-d6, 300 MHz) δ 10.35 (1H, br s), 7.90 (1H, dd, J=1.25, 7.75 Hz), 7.68 (1H, m), 7.41 (2H, m), 5.92 (1H, s), 4.32 (2H, t, J=5.75 Hz), 3.27 (2H, m), 2.80 (6H, s), 2.25 (2H, m); MS (ESI, Pos.) calcd for $C_{14}H_{17}NO_3$ m/z [M+H]=248.1, found 248.1.

Method C.

EXAMPLE 3

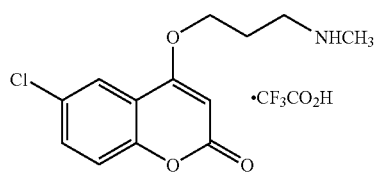

6-Chloro-4-(3-methylamino-propoxy)-1-benzopyran-2-one Trifluoroacetic acid salt 6-Chloro-4-hydroxycoumarin (0.747 mmol, 0.147 g), $PPh_3$ (0.785 mmol, 0.206 g), and (3-hydroxypropyl)-methylcarbamic acid tert-butyl ester (0.785 mmol, 0.148 g) is suspended in 5 mL THF and is cooled to 0° C. DIAD (0.822 mmol, 0.161 mL) is added dropwise at 0° C., and then the mixture is warmed to ambient temperature and is stirred for 6 hrs. The THF is removed under reduced pressure. Neat TFA is added and the solution is mixed at ambient temperature for 30 min-1 hr. The TFA is evaporated, $Et_2O$ is added and the resulting precipitate is filtered. (Alternatively the $Et_2O$ trituration step may be omitted). The crude material is further purified by HPLC to afford the title compound as the trifluoroacetic acid salt (54.5 mg, 19%) $^1$H NMR (DMSO-d6, 300 MHz) δ 8.41 (2H, br s), 7.87 (1H. d, J=2.5 Hz), 7.73 (1H, dd, J=2.75, 9 Hz), 7.48 (1H, d, J=9 Hz), 5.99 (1H, s), 4.30 (2H, t, J=5.75 Hz), 3.14 (2H, m), 2.63 (3H, t, J=5.5 Hz), 2.14 (2H, m); MS (ESI, Pos.) calcd for $C_{13}H_{14}ClNO_3$ m/z [M+H]=268.1, found 268.2.

EXAMPLE 4

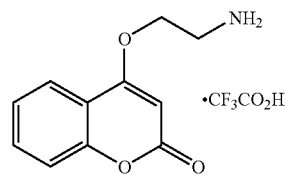

4-(2-Amino-ethoxy)-1-benzopyran-2-one Trifluoroacetic acid salt

Is prepared via method A at 0° C from 4-hydroxycoumarin and (2-hydroxyethyl)carbamic acid tert-butyl ester to afford the title compound as the trifluoroacetic acid salt (250 mg, 59.0%). $^1$H NMR (DMSO-d6, 300 MHz) δ 8.13 (1H, dd, J=1.5, 8 Hz), 8.09 (2H, br s), 7.69 (1H, m), 7.40 (2H, m), 5.99 (1H, s), 4.40 (2H, t, J=4.75 Hz), 3.36 (2H, buried under solvent peak); MS (ESI, Pos.) calcd for $C_{11}H_{11}NO_3$ m/z [M+H]=206.1, found 206.1.

EXAMPLE 5

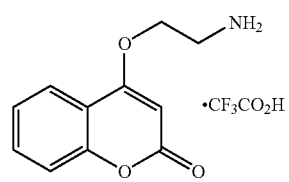

4-(2-Amino-ethoxy)4-chloro-1-benzopyran-2-one Trifluoroacetic acid salt

Is prepared via method A at 0° C. from 6-choro-4-hydroxycoumarin and (2-hydroxyethyl)-carbamic acid tert-butyl ester to afford the title compound as the trifluoroacetic acid salt (35.8 mg, 9.9%); %); $^1$H NMR (DMSO-d6, 300 MHz) δ 8.21 (1H, d, J=2.5 Hz), 8.05 (2H, br s), 7.72 (1H, dd, J=2.5, 9 Hz), 7.47 (1H, d, J=8.75 Hz), 6.07 (1H, s), 4.39 (2H, t, J=4.75 Hz), 3.33 (2H, buried under solvent peak); MS (ESI, Pos.) calcd for $C_{11}H_{10}ClNO_3$ m/z [M+H]=240.0, found 240.1.

EXAMPLE 6

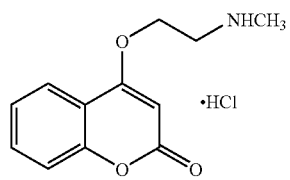

4-(2-Methylamino-ethoxy)-1-benzopyran-2-one Hydrochloric acid salt

4-Hydroxycoumarin (1.33 mmol, 0.216 g) is dissolved in 10 mL of THF. Triphenylphosphine (1.4 mmol, 0.367 g) and (2-hydroxyethyl)-methyl-carbamic acid tert-butyl ester (1.44 mmol, 0.250 g) is added and the solution is cooled to 0° C. DIAD (1.46 mmol, 0.287 mL) is added dropwise at 0° C., and the solution is stirred 15 min. at 0° C. The reaction is allowed to warm to ambient temperature and is stirred overnight. The solvent is evaporated under reduced pressure, the product is dissolved in neat TFA (10 ml), and the solution is stirred at ambient temperature for 30 min. The reaction mixture is concentrated in vacuo and is treated with a HCl/MeOH solution followed by Et$_2$O precipitation to generate the title compound as the hydrochloric acid salt which is filtered, is washed with Et$_2$O, and is dried (75 mg, 22.1%). $^1$H NMR (DMSO-d6, 300 MHz) δ 9.03 (2H, s), 8.15 (1H, dd, J=1.5, 7.75 Hz), 7.69 (1H, m), 7.40 (2H, m), 6.00 (1H, s), 4.49 (2H, t, J=4.75 Hz), 3.45 (2H, t J=4.5 Hz), 2.67 (3H, s); MS (ESI, Pos.) calcd for C$_{12}$H$_{13}$NO$_3$ m/z [M+H]=220.1, found 220.1.

EXAMPLE 7

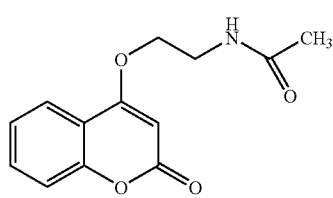

N-[2-(2-Oxo-2H-1-benzopyran-4-yloxy)-ethyl]-acetamide 4-(2-Amino-ethoxy)-1-benzopyran-2-one trifluoroacetate (10) (0.157 mmol, 0.050 g) is dissolved in 5 mL of DCM. Pyridine is added (0.314 mmol, 25.4 µL) followed by acetic anhydride (0.314 mmol, 29.6 µL) and the reaction is stirred at ambient temperature for 4 hours. The reaction mixture is concentrated in vacuo and the residue is purified by reversed-phase HPLC to afford the title compound as the trifluoroacetic acid salt (31.4 mg, 81%). $^1$H NMR (DMSO-d6, 300 MHz) δ 8.19 (1H, br t), 7.91 (1H, dd, J=1.5, 7.75 Hz), 7.67 (1H, m), 7.38 (2H, m), 5.91 (1H, s), 4.20 (2H, t, J=5.5 Hz), 3.52 (2H, m), 1.84 (3H, s); MS (ESI, Pos.) calcd for C$_{13}$H$_{13}$NO$_4$ m/z [M+H]=248.1, found 248.0.

EXAMPLE 8

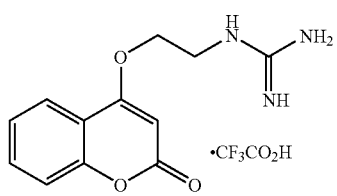

N-[2-(2-Oxo-2H-1-benzopyran-4-yloxy)-ethyl]-guanidine Trifluoroacetic acid salt 4-(2-Amino-ethoxy)-1-benzopyran-2-one trifluoroacetate (0.313 mmol, 100 mg) is placed in a small vial along with 2 mL of acetonitrile. Diisopropylethylamine is added dropwise until the pH of the solution is ~9 by pH paper. N,N'-Bis(tert-butoxycarbonyl)-1-H-pyrazole-1-carboxamidine (0.24 mmol, 74.5 mg) is added and the reaction is mixed at ambient temperature for 5 hrs. The reaction mixture is concentrated in vacuo, then is redissolved in neat TFA and is stirred at ambient temperature for 30 min. The TFA is removed under reduced pressure and the residue is purified by reversed-phase HPLC to afford the title compound as the trifluoroacetic acid salt (35.0 mg, 31%). $^1$H NMR (DMSO-d6, 300 MHz) δ 7.88 (1H, dd, J=1.5, 8 Hz), 7.81 (1H, br t), 7.68 (1H, m), 7.39 (2H, m), 7.28 (3H, br s), 5.49 (1H, s), 4.30 (2H, t, J=5 Hz), 3.67 (2H, q, J=5.5 Hz); MS (ESI, Pos.) calcd for C$_{12}$H$_{13}$N$_3$O$_3$ m/z [M+H]=248.1, found 248.1.

EXAMPLE 9

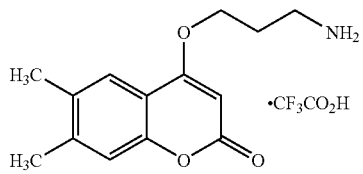

4-(3-Amino-propoxy)-6,7-dimethyl-1-benzopyran-2-one Trifluoroacetic acid salt Is prepared via method A at 0° C. from 6,7-dimethyl-4-hydroxycoumarin and (3-hydroxypropyl)-carbamic acid tert-butyl ester to afford the title compound as the trifluoroacetic acid salt (57.0 mg, 11%). $^1$H NMR (DMSO-d6, 300 MHz) δ 7.78 (2H, br s), 7.59 (1H, s), 7.23 (1H, s), 5.81 (1H, s), 4.28 (2H, t, J=6 Hz), 3.04 (2H, m), 233 (3H, s), 2.29 (3H, s), 2.11 (2H, m); MS (ESI, Pos.) calcd for C$_{14}$H$_{17}$NO$_3$ m/z [M+H]=248.1, found 248.2.

EXAMPLE 10

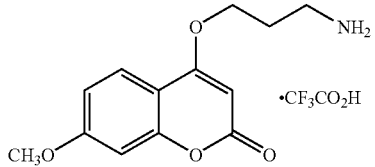

4-(3-Amino-propoxy)-7-methoxy-1-benzopyran-2-one Trifluoroacetic acid salt

Is prepared via method A at 0° from 7-methoxy-4-hydroxycoumarin and (3-hydroxypropyl)-carbamic acid tert-butyl ester to afford the title compound as the trifluoroacetic acid salt (167.9 mg, 32%). $^1$H NMR (DMSO-d6, 300 MHz) δ 7.77(2H, br s), 7.75 (1H, d, J=8.75 Hz), 7.01 (1H, d, J=2.5 Hz), 6.96 (1H, dd, J=2.25, 8.75 Hz), 5.75 (1H, s), 4.28 (2H, t, J=6 Hz), 3.86 (3H, s), 3.02 (2H, m), 2.10 (2H, m); MS (ESI, Pos.) calcd for C$_{13}$H$_{15}$NO$_4$ m/z [M+H]=250.1, found 250.1.

EXAMPLE 11

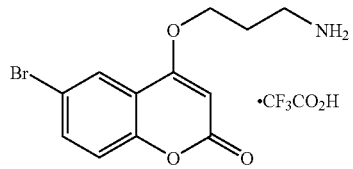

4-(3-Amino-propoxy)-6-bromo-1-benzopyran-2-one Trifluoroacetic acid salt

Is prepared via method C from 6-bromo-4-hydroxycoumarin and (3-hydroxypropyl)-carbamic acid tert-butyl ester to afford the title compound as the trifluoroacetic acid salt (64.6 mg, 25%). $^1$H NMR (DMSO-d6, 300 MHz) δ 7.98 (1H, d, J=2.5 Hz). 7.84 (1H, dd, J=2.5, 9 Hz), 7.76 (2H, br s). 7.40 (1H, d, J=9 Hz), 5.97 (1H, s), 4.30 (2H, t, J=5.75 Hz), 3.04 (2H, br s), 2.11 (2H, m); MS (ESI, Pos.) calcd for C$_{12}$H$_{12}$BrNO$_3$ m/z [M+H]=298.0, found [no parent obs].

EXAMPLE 12

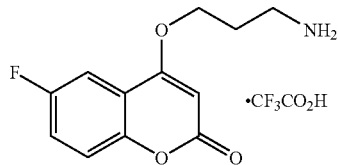

4-(3-Amino-propoxy)-6-fluoro-1-benzopyran-2-one Trifluoroacetic acid salt

Is prepared via method A at 0° C. from 6-fluoro-4-hydroxycoumarin and (3-hydroxypropyl)-carbamic acid tert-butyl ester to afford the title compound as the trifluoroacetic acid salt (264 mg, 90%) $^1$H NMR (DMSO-d6, 300 MHz) δ 7.79 (2H, br s), 7.67 (1H, dd, J=2.75, 8.75 Hz), 7.52 (2H, m), 5.97 (1H, s), 4.30 (2H, t, J=5.5 Hz), 3.05 (2H, br s), 2.10 (2H, m); MS (ESI, Pos.) calcd for C$_{12}$H$_{12}$FNO$_3$ m/z [M+H]=238.1, found 238.2.

EXAMPLE 13

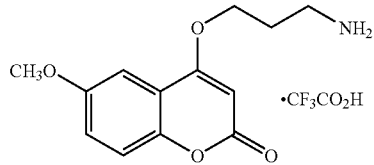

4-(3-Amino-propoxy)-6-methoxy-1-benzopyran-2-one Trifluoroacetic acid salt

Is prepared via method A at 0° C. from 6-methoxy-4-hydroxycoumarin and (3-hydroxypropyl)-carbamic acid tert-butyl ester to afford the title compound as the trifluoroacetic acid salt (195 mg, 65%). $^1$H NMR (DMSO-d6, 300 MHz) δ 7.77 (2H, br s), 7.32 (3H, m), 5.90 (1H, s), 4.31 (2H, t, J=6 Hz), 3.83 (3H, s), 3.04 (2H, t, J=7.25 Hz), 2.12 (2H, m); MS (ESI, Pos.) calcd for C$_{13}$H$_{15}$NO$_4$ m/z [M+H]=250.1, found 250.2.

EXAMPLE 14

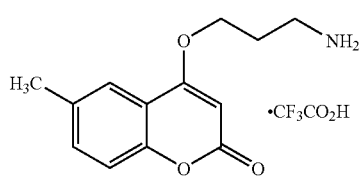

4-(3-Amino-propoxy)-6-methyl-1-benzopyran-2-one Trifluoroacetic acid salt

Is prepared via method A at 0° C. from 6-methyl-4-hydroxycoumarin and (3-hydroxypropyl)-carbamic acid tert-butyl ester to afford the title compound as the trifluoroacetic acid salt (298 mg, 94%). $^1$H NMR (DMSO-d6, 300 MHz) δ 7.80 (2H, br s), 7.65 (1H, brd), 7.49 (1H, dd, J=2, 8.5 Hz), 7.31 (1H, d, J=8.5 Hz), 5.87 (1H, s), 4.30 (2H, t, J=6 Hz), 3.04 (2H, m), 2.39 (3H, s), 2.10 (2H, m); MS (ESI, Pos.) calcd for C$_{13}$H$_{15}$NO$_3$ m/z [M+H] 234.1, found 234.2.

EXAMPLE 15

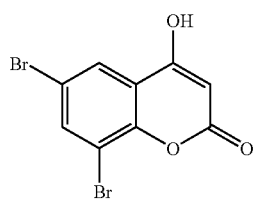

6,8-Dibromo-4-hydroxy-1-benzopyran-2-one

A solution is prepared of diethylcarbonate (62.5 mmol, 7.6 mL) in 150 mL of toluene to which is added NaH (37.5 mmol, 1.5 g of 60% dispersion in mineral oil) in portions. To this solution is added, dropwise, 3',5'-dibromo-2'-hydroxyacetophenone (12.5 mmol, 3.67 g) in 50 mL of toluene. The reaction is heated to 105° C. overnight, cooled to ambient temperature, 100 mL of 1N NaOH, is added and the reaction is stirred vigorously for 5 hrs at ambient temperature. The layers are separated and the aqueous layer is washed with EtOAc 2×. The combined organic layers are washed with H$_2$O 1×. The combined aqueous layers are acidified to pH 2 with conc HCl to form a precipitate that is filtered and is washed with H$_2$O. The solid material is dissolved in ACN/H$_2$O and speed vacced to dryness to afford the title compound as a light tan solid (0.737 g, 18%). $^1$H NMR (DMSO-d6, 300 MHz) δ 12.98 (1H, br s), 8.18 (1H, d, J=2.25 Hz), 7.90 (1H, d, J=2.25 Hz), 5.64 (1H, s); MS (ESI, Pos.) calcd for C$_9$H$_4$Br$_2$O$_3$ m/z [M+H]=318.9, found 318.9.

EXAMPLE 16

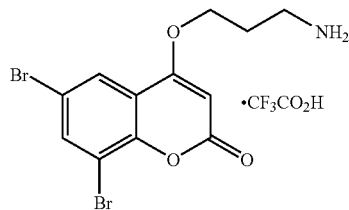

4-(3-Amino-propoxy)-6,8-dibromo-1-benzopyran-2-one Trifluoroacetic acid salt

Is prepared via method A at 0° C. from 6,8-dibromo-4-hydroxycoumarin and (3-hydroxypropyl)-carbamic acid tert-butyl ester. The Boc protected intermediate is HPLC purified prior to treatment with TFA. The title compound is obtained as the trifluoroacetic acid salt by reversed-phase HPLC purification (38.2 mg, 16.0%). $^1$H NMR (DMSO-d6, 300 MHz) δ 8.23 (1H, d, J=2.25 Hz), 7.99 (1H, d, J=2.25 Hz), 7.75 (2H, brs), 6.03 (1H, s), 4.31 (2H, t, J=5.75 Hz), 3.04 (2H, m), 2.11 (2H, m); MS (ESI, Pos.) calcd for C$_{12}$H$_{11}$Br$_2$NO$_3$ m/z [M+H]=378.0, found 378.0

EXAMPLE 17

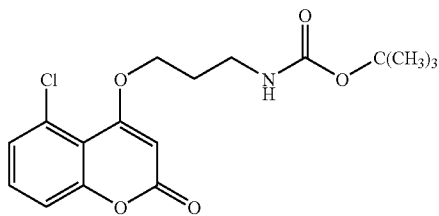

[3-(5-Chloro-2-oxo-2H-1-benzopyran-4-yloxy)-propyl]-carbamic acid tert-butyl ester A solution of triphenylphosphine (0.438 g, 1.67 mmol) in 10 mL of THF is cooled to −78° C. and DIAD (0.430 g) is added in one portion. (3-Hydroxy-propyl)-carbamic acid tert-butyl ester (560 mg, 1.3 eq) in 1 mL of THF is added and the solution is allowed to warm to room temperature over the course of 1 hr. The yellow solution is treated with 5-chloro-4-hydroxycoumarin (0.300 g, 1.5 mmol) and is stirred at ambient temperature for 3.5 hrs. The solvent is removed under reduced pressure and the crude product is purified using an ISCO 4 g SiO$_2$ column eluting with ether/heptane gradient to afford the title compound (0.106 g, 20%). $^1$H NMR (CDCl$_3$, 300 MHz) δ 7.27 (3H, m), 5.71 (1H, s), 4.73 (1H, brs), 4.17 (2H, t, J=5.75 Hz), 3.41 (2H, q, J=6.5 Hz), 2.13 (2H, m), 1.43 (9H, s); MS (ESI, Pos.) calcd for C$_{17}$H$_{20}$ClNO$_5$ m/z [M+H+Na]=376.1, found 376.1.

EXAMPLE 18

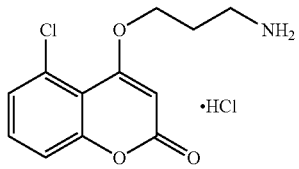

4-(3-Amino-propoxy)-5-chloro-1-benzopyran-2-one Hydrochloric acid salt

[3-(5-Chloro-2-oxo-2H-1-benzopyran-4-yloxy)-propyl]-carbamic acid tert-butyl ester (24a) (0.079 g, 0.22 mmol) is treated with 4N HCl/dioxane for several minutes during which time a precipitate is formed. The solventVHCl is removed under reduced pressure. The residue is recrystallized from MeOH/EtOAc followed by a second recrystallization from EtOH to afford the title compound as the hydrochloric acid salt (22.8 mg, 41%). $^1$H NMR (DMSO-d6, 300 MHz) δ 7.94 (3H, brs), 7.62 (1H, t, J=8.25 Hz), 7.43 (2H, m), 5.94 (1H, s), 4.29 (2H, t, J=5.75 Hz), 3.04 (2H, t, J=7 Hz), 2.14 (2H, m); MS (ESI, Pos.) calcd for C$_{12}$H$_{12}$ClNO$_3$ m/z [M+H]=254.0, found 254.1.

EXAMPLE 19

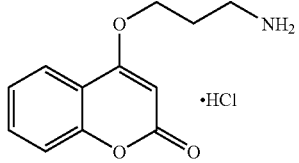

4-(3-Amino-propoxy)-1-benzopyran-2-one Hydrochloric acid salt

Is prepared via method B from 4-hydroxycoumarin and (3-hydroxy-propyl)-carbamic acid tert-butyl ester to afford the title compound as the hydrochloric acid salt (0.210 g, 50.0%).%). $^1$H NMR (DMSO-d6, 300 MHz) δ 8.03 (2H, br s), 7.88 (1H, dd, J=1.5, 8 Hz), 7.68 (1H, m), 7.39 (2H, m), 5.91 (1H,s), 4.32 (2H, t, J=6 Hz), 3.02 (2H, m), 2.15 (2H, m); MS (ESI, Pos.) calcd for C$_{12}$H$_{13}$NO$_3$ m/z [M+H]=220.1, found 220.1.

EXAMPLE 20

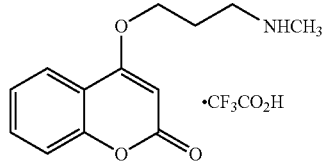

4-(3-Methylamino-propoxy)-1-benzopyran-2-one
Trifluoroacetic acid salt

Is prepared via method A at 0° C. from 4-hydroxycoumarin and (3-hydroxypropyl)-methyl-carbamic acid tert-butyl ester to afford the title compound as the trifluoroacetic acid salt (0.380 g, 73.0%). $^1$H NMR (DMSO-d6, 300 MHz) δ 8.47 (2H, br s), 7.89 (1H, dd, J=1.5, 8 Hz), 7.68 (1H, m), 7.40 (2H, m), 5.91 (1H, s), 4.31 (2H, t, J=5.75 Hz), 3.14 (2H, t, J=7.25 Hz), 2.64 (3H, s), 2.15 (2H, m); MS (ESI, Pos.) calcd for $C_{13}H_{15}NO_3$ m/z [M+H]=234.1, found 234.1.

EXAMPLE 21

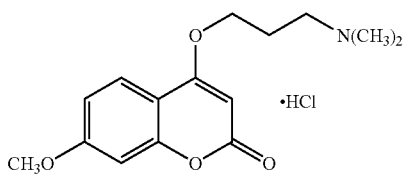

4-(3-Dimethylamino-propoxy)-7-methoxy-1-benzopyran-2-one Hydrochloric acid salt

Is prepared via method B from 7-methoxy-4-hydroxycoumarin and 3-dimethylamino-propan-1-ol using 4M HCl in dioxane to form the title compound as the Hydrochloric acid salt (292 mg, 65.0%). $^1$H NMR (DMSO-d6, 300 MHz) δ 10.21 (1H, s), 7.79 (1H, d, J=8.75 Hz), 7.01 (1H, d, J=2.25 Hz), 6.95 (1H, dd, J=2.25, 8.75 Hz), 5.76 (1H, s), 4.28 (2H, t, J=6 Hz), 3.86 (3H, s), 3.26 (2H, m), 2.8 (6H, s), 2.22 (2H, m); MS (ESI, Pos.) calcd for $C_{15}H_{19}NO_4$ m/z [M+H]=278.1, found 278.2.

EXAMPLE 22

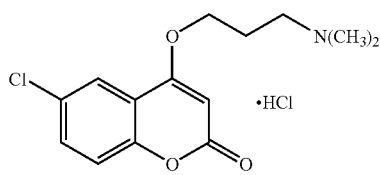

6-Chloro-4-(3-dimethylamino-propoxy)-1-benzopyran-2-one Hydrochloric acid salt

Is prepared via method B from 6-chloro-4-hydroxycoumarin and 3-dimethylamino-propan-1-ol using 4M HCl in dioxane to form the title compound as the hydrochloric acid salt (332 mg, 73%). $^1$H NMR (DMSO-d6, 300 MHz) δ 10.23 (1H, s), 7.88 (1H, d, J=2.75 Hz), 7.73 (1H, dd, J=2.75, 9 Hz), 7.48 (1H, d, J=9Hz), 6.0 (1H, s), 4.31 (2H, t, J=5.75 Hz), 3.28 (2H, m), 2.80 (3H, s), 2.80 (3H, s), 2.24 (2H, m); MS (ESI, Pos.) calcd for $C_{14}H_{16}ClNO_3$ m/z [M+H]=282.1, found 282.1.

EXAMPLE 23

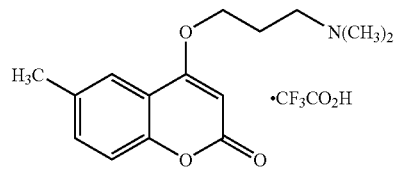

4-(3-Dimethylamino-propoxy)-6-methyl-1-benzopyran-2-one Trifluoroacetic acid salt Is prepared via method A at 0° C. from 6-methyl-4-hydroxycoumarin and 3-dimethylamino-propan-1-ol. The crude product is purified by HPLC to afford the title compound as the trifluoroacetic acid salt (151 mg, 28.1%). $^1$H NMR (DMSO-d6, 300 MHz) δ 9.54 (1H, br s), 7.64 (1H, br s), 7.49 (1H, dd, J=1.75, 8.5 Hz), 7.31 (1H, d, J=8.5 Hz), 5.90 (1H, s), 4.29 (2H, t, J=5.75 Hz), 3.29 (2H, m), 2.86 (3H, s), 2.84 (3H, s), 2.4 (3H, s), 2.22 (2H, m); MS (ESI, Pos.) calcd for $C_{15}H_{19}NO_3$ m/z [M+H]=262.1, found 262.2.

EXAMPLE 24

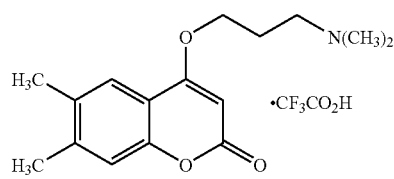

4-(3-Dimethylami no-propoxy)-6,7-dimethyl-1-benzopyran-2-one Trifluoroacetic acid salt Is prepared via method A 0° C. from 6,7-dimethy-4-hydroxycoumarin and 3-dimethylamino-propan-1-ol. The crude product is purified by HPLC to afford the title compound as the trifluoroacetic acid salt (63.6 mg, 15.6%). $^1$H NMR (DMSO-d6, 300 MHz) δ 9.52 (1H, s), 7.59 (1H, s), 7.23 (1H, s), 5.83 (1H, s), 4.28 (2H, t, J=6 Hz), 3.29 (2H, m), 2.84

(3H, s), 2.85 (3H, s) 2.31 (6H, 2), 2.20 (2H, m); MS (ESI, Pos.) calcd for $C_{16}H_{21}NO_3$ m/z [M+H]=276.2, found 276.2.

EXAMPLE 25

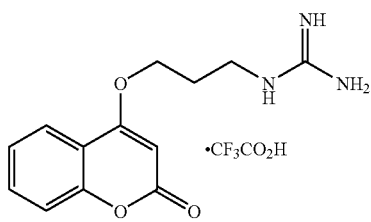

N-[3-(2-Oxo-2H-1-benzopyran-4-yloxy)-propyl] guanidine Trifluoroacetic acid salt Is prepared according to the procedure for N-[2-(2-oxo-2H-1-benzopyran-4-yloxy)-ethyl]-guanidine from the trifluoroacetic acid salt of 4-(3-amino-propoxy)-1-benzopyran-2-one to afford the title compound as the trifluoroacetic acid salt after HPLC purification (40.0 mg, 35%). $^1$H NMR (DMSO-d6, 300 MHz) δ 7.88 (1H, dd, J=1.5, 8 Hz), 7.67 (2H, m), 7.39 (2H, m), 7.15 (3H, br s), 5.92 (1H, s ), 4.26 (2H, t, J=6 Hz), 3.32 (2H, buried under solvent peak), 2.03 (2H, m); MS (ESI, Pos.) calcd for $C_{13}H_{15}N_3O_3$ m/z [M+H]=262.1, found 262.1.

EXAMPLE 26

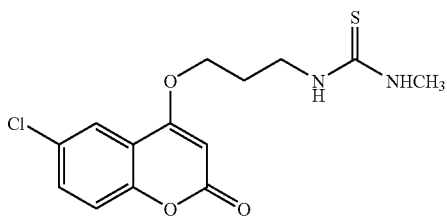

1-[3-(6-Chloro-2-oxo-2H-1-benzopyran-4-yloxy)-propyl]-3-methyl-thiourea 6-chloro-4-(3-methylamino-propoxy)-1-benzopyran-2-one trifluoroacetic acid salt (0.272 mmol, 100 mg) is suspended in 5 mL of 1:1 DMF:DCM. DIEA is added dropwise until pH=9 by pH paper. Methyl isothiocyanate (0.299 mmol, 0.022 g) is added and the reaction is stirred at ambient temperature for 3 hrs. The reaction mixture is concentrated in vacuo and the crude material is purified by reversed-phase HPLC to afford the title compound (66.1 mg, 78.7%). $^1$H NMR (DMSO-d6, 300 MHz) δ 7.85 (1H, d, J=2.5 Hz), 7.71 (1H, dd, J=2.75, 9 Hz), 7.55 (1H, br m), 7.46 (1H, d, J=9 Hz), 5.95 (1H, s), 4.24 (2H, t, J=5.75 Hz), 3.59 (2H, br s), 2.79 (3H, br s), 2.07 (2H, m); MS (ESI, Pos.) calcd for $C_{14}H_{15}ClN_2O_3S$ m/z [M+H]=327.0, found 327.0.

EXAMPLE 27

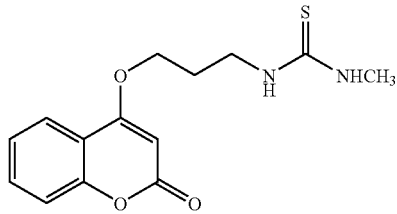

1-Methyl-3-[3-(2-oxo-2H-1-benzopyran-4-yloxy)-propyl]-thiourea)

Is prepared according to the procedure for 1-[3-(6-chloro-2-oxo-2H-1-benzopyran-4-yloxy)-propyl]-3-methyl-thiourea from 4-(3-amino-propoxy)-1-benzopyran-2-one (trifluoroacetic acid salt) to afford the title compound after HPLC purification (71 mg, 73%). $^1$H NMR (DMSO-d6, 300 MHz) δ 7.87 (1H, dd, J=1.5, 7.75 Hz), 7.67 (1H, m), 7.56 (1H, br s), 7.39 (3H, m), 5.88 (1H, s), 4.24 (2H, t, J=6 Hz), 3.59 (2H, s), 2.79 (3H, s), 2.07 (2H, m); MS (ESI, Pos.) calcd for $C_{14}H_{16}N_2O_3S$ m/z [M+H]=292.1, found 292.4.

EXAMPLE 28

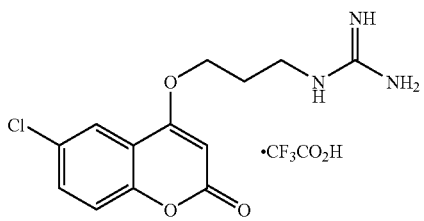

N-[3-(6-Chloro-2-oxo-2H-1-benzopyran-4-yloxy)-propyl]guanidine Trifluoroacetic acid salt 6-Chloro-4-(3-methylamino-propoxy)-1-benzopyran-2-one trifluoroacetic acid salt (200 mg, 0.543 mmol) is suspended in 7 mL of DCM. Diisopropylethylamine is added dropwise until pH=9 by pH paper. N,N'-Bis(tert-butoxycarbonyl)-1-H-pyrazole-1-carboxamidine (169 mg, 0.543 mmol) is added and is stirred at ambient temperature overnight. The reaction mixture is concentrated in vacuo and Et$_2$O is added to form a white precipitate, which is filtered and is washed with Et$_2$O. The crude material is treated with neat TFA (10 mL) for 30 min at ambient temperature. The TFA is removed under reduced pressure. Et$_2$O is added to precipitate the product, which is filtered, is washed with Et$_2$O, and is dried. The crude material is further purified by reversed-phase HPLC to afford the title compound as the trifluoroacetic acid salt. (108 mg, 48.6%). %). $^1$H NMR (DMSO-d6, 300 MHz) δ 7.86 (1H, d, J=2.5 Hz), 7.72 (1H, dd, J=2.5, 8.75 Hz), 7.64 (1H, t, J=5.5 Hz), 7.47 (1H, d, J=8.75 Hz), 7.12 (3H, br s), 6.00 (1H, s), 4.26 (2H, t, J=5.75 Hz), 3.36 (2H, m, J=6.25 Hz), 2.04 (2H, m, J=6.25 Hz); MS (ESI, Pos.) calcd for $C_{13}H_{14}ClN_3O_3$ m/z [M+H]=296.1, found 296.0.

EXAMPLE 29

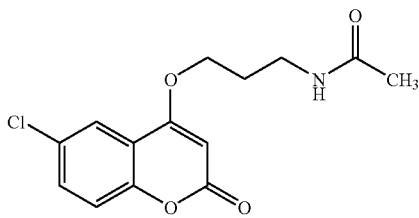

N-[3-(6-Chloro-2-oxo-2H-1-benzopyran-4-yloxy)-propyl]-acetamide 6-chloro-4-(3-methylamino-propoxy)-1-benzopyran-2-one trifluoroacetic acid salt (0.272 mmol, 100 mg) is suspended in 3 mL of DCM. DIEA (0.544 mmol, 95 μL) is added followed by acetic anhydride (0.816 mmol, 77.1 EL). After stirring for 1 hr at ambient temperature, the reaction mix is concentrated in vacuo and purified by reversed-phase HPLC to afford the title compound (39.0 mg, 49%). $^1$H NMR (DMSO-d6, 300 MHz) δ 7.95 (1H, br t), 7.79 (1H, d, J=2.5 Hz), 7.72 (1H, dd, J=2.5, 8.75 Hz), 7.46 (1H, d, J=8.75 Hz), 5.95 (1H, s), 4.23 (2H, t, J=6 Hz), 3.24 (2H, q, J=6 Hz), 1.95 (2H, m, J=6.25 Hz), 1.80 (3H, s); MS (ESI, Pos.) calcd for $C_{14}H_{14}ClNO_4$ m/z [M+H]=296.1, found 296.2.

EXAMPLE 30

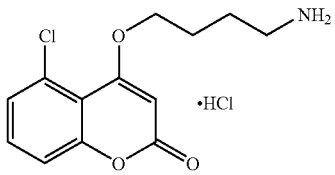

4-(4-Amino-butoxy)-5-chloro-1-benzopyran-2-one Hydrochloric acid salt

Is prepared using the procedure for 4-(3-amino-propoxy)-5-chloro-1-benzopyran-2-one from [3-(5-chloro-2-oxo-2H-1-benzopyran-4-yloxy)-butyl]-carbamic acid tert-butyl ester to afford the title compound as the hydrochloric acid salt. $^1$H NMR (DMSO-d6, 300 MHz) δ 7.86 (3H, br s), 7.61 (1H, t, J=8.25 Hz), 7.42 (2H, t, J=9.5, 8.75 Hz), 5.96 (1H, s), 4.23 (2H, t, J=5.75 Hz), 2.85 (2H, m), 1.83 (4H, m); MS (ESI, Pos.) calcd for $C_{13}H_{14}ClNO_3$ m/z [M+H]=268.1, found 268.1.

EXAMPLE 31

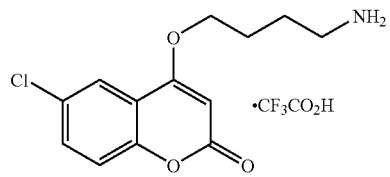

4-(4-Amino-butoxy)-6-chloro-1-benzopyran-2-one Trifluoroacetic acid salt

Is prepared via method A at 0° C. from and 6-chloro-4-hydroxycoumarin and (4-hydroxy-butyl)-carbamic acid tert-butyl ester to afford the title compound as the trifluoroacetic acid salt (185 mg, 59%). $^1$H NMR (DMSO-d6, 300 MHz) δ 7.74 (4H, m), 7.47 (1H, d, J=9 Hz), 6.00 (1H, s), 4.26 (2H, t, J=5.75 Hz), 2.89 (2H, m), 1.87 (2H, m), 1.74 (2H, m) MS (ESI, Pos.) calcd for $C_{13}H_{14}ClNO_3$ m/z [M+H]=268.1, found 268.2.

EXAMPLE 32

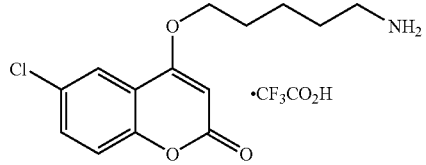

4-(5-Amino-pentyloxy)-6-chloro-1-benzopyran-2-one Trifluoroacetic acid salt

Is prepared via method A at 0° C. from 6-chloro-4-hydroxycoumarin and (5-hydroxy-pentyl)-carbamic acid tert-butyl ester to afford the title compound as the trifluoroacetic acid salt (72.0 mg, 36%). $^1$H NMR (DMSO-d6, 300 MHz) δ 7.77 (1H, d, J=2.75 Hz), 7.72 (1H, dd, J=2.5, 8.75 Hz), 7.65 (2H, br s), 7.47 (1H, d, J=8.75 Hz), 5.99 (1H, s), 4.23 (2H, t, J=6.25 Hz), 2.83 (2H, m), 1.83 (2H, m), 1.62 (2H, m), 1.52 (2H, m); MS (ESI, Pos.) calcd for $C_{14}H_{16}ClNO_3$ m/z [M+H]=282.1, found 282.1.

EXAMPLE 33

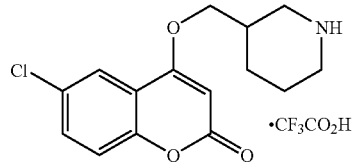

6-Chloro-4-(piperidin-3-ylmethoxy)-1-benzopyran-2-one Trifluoroacetic acid salt Is prepared via method A at 0° C. from 6-chloro-4-hydroxycoumarin and (3-hydroxymethyl-cyclohexyl)-carbamic acid tert-butyl ester to afford the title compound as the trifluoroacetic acid salt after HPLC purification (68.1 mg, 23%). $^1$H NMR (DMSO-d6, 300 MHz) δ 8.62 (1H, m), 8.35 (1H, m), 7.87 (1H, d, J=2.75 Hz), 7.73 (1H, dd, J=2.5, 8.75 Hz), 7.48 (1H, d, J=9 Hz), 6.00 (1H, s), 4.16 (2H, m), 3.27 (2H, d, J=13 Hz), 2.88 (2H, m), 2.27 (1H, m), 1.86 (2H, m), 1.67 (1H, m), 1.44 (1H, m); MS (ESI, Pos.) calcd for $C_{15}H_{16}ClNO_3$ m/z [M+H]=294.1, found 294.2.

EXAMPLE 34

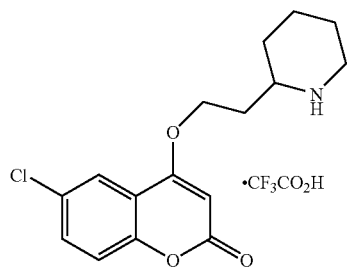

6-Chloro-4-(2-piperidin-2-yl-ethoxy)-1-benzopyran-2-one Trifluoroacetic acid salt Is prepared via method C at 0° C. from 6-chloro-4-hydroxycoumarin and 2-(2-hydroxy-ethyl)-piperidine-1-carboxylic acid tert-butyl ester to afford the title compound as the trifluoroacetic acid salt after HPLC purification (43.7 mg, 20.7%). $^1$H NMR (DMSO-d6, 300 MHz) δ 8.55 (1H, br s), 8.36 (1H, br s), 7.87 (1H, d, J=2.5 Hz), 7.73 (1H, dd, J=2.5, 8.75 Hz), 7.48 (1H, d, J=8.75 Hz), 5.99 (1H, s), 4.32 (2H, m), 3.28 (2H, d, J=11.75 Hz), 2.91 (1H, m), 2.10 (4H, m), 1.76 (2H, brd), 1.48 (2H, m); MS (ESI, Pos.) calcd for $C_{16}H_{18}ClNO_3$ m/z [M+H]=308.1, found 308.2.

EXAMPLE 35

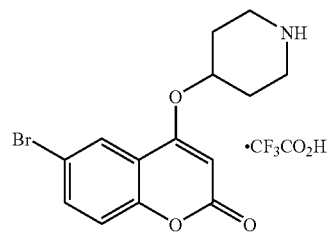

6-Bromo-4-(piperidin-4-yloxy)-1-benzopyran-2-one Trifluoroacetic acid salt

Is prepared via method A at 0° C. from 6-bromo-4-hydroxycoumarin and 4-hydroxy-piperidine-1-carboxylic acid tert-butyl ester to afford the trifluoroacetic acid salt (47.3 mg, 25.3%). $^1$H NMR (DMSO-d6, 300 MHz) δ 8.46 (2H, br s), 8.01 (1H, d, J=2.25 Hz), 7.84 (1H, dd, J=2.5, 8.75 Hz), 7.41 (1H, d, J=9 Hz), 6.14 (1H, s), 4.97 (1H, m), 3.32 (2H, buried under solvent peak), 3.14 (2H, m), 2.12 (2H, m), 2.01 (2H, m); MS (ESI, Pos.) calcd for $C_{14}H_{14}BrNO_3$ m/z [M+H]=324.0, found 324.0.

EXAMPLE 36

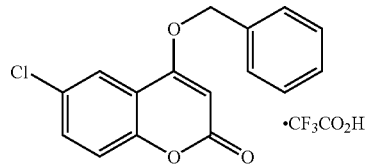

6Chloro-4-(pyridin-2-ylmethoxy)-1-benzopyran-2-one Trifluoroacetic acid salt Is prepared via method B from 6-chloro-4-hydroxycoumarin and pyridin-2-yl-methanol to afford the title compound as the trifluoroacetic acid salt after HPLC purification (36.0 mg, 16.8%). $^1$H NMR (DMSO-d6, 300 MHz) δ 8.63 (1H, m), 7.94 (1H, m), 7.83 (1H, d, J=2.5 Hz), 7.72 (2H, m), 7.47 (2H, m), 6.13 (1H, s), 5.45 (2H, s); MS (ESI, Pos.) calcd for $C_{15}H_{10}ClNO_3$ m/z [M+H]=288.0, found 287.9.

EXAMPLE 37

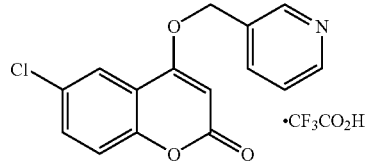

6-Chloro-4-(pyridin-3-ylmethoxy)-1-benzopyran-2-one Trifluoroacetic acid salt Is prepared via method B from 6-chloro-4-hydroxycoumarin and pyridin-3-yl-methanol using HCl/dioxane to form the hydrochloric acid salt which is then purified by HPLC to afford the title compound as the trifluoroacetic acid salt (45.0 mg, 21.0%). $^1$H NMR (DMSO-d6, 300 MHz) δ 8.86 (1H, s), 8.70 (1H, d, J=5 Hz), 8.17 (1H, d, J=8 Hz), 7.80 (1H, d, J=2.5 Hz), 7.73 (1H, dd, J=2.5, 8.75 Hz), 7.66 (1H, m), 7.49 (1H, d, J=9 Hz), 6.17 (1H, s), 5.46 (2H, s); MS (ESI, Pos.) calcd for $C_{15}H_{10}ClNO_3$ m/z [M+H]=288.0, found 287.9.

EXAMPLE 38

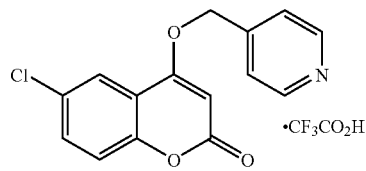

6-Chloro-4-(pyridin-4-ylmethoxy)-1-benzopyran-2-one Trifluoroacetic acid salt Is prepared via method B from 6-chloro-4-hydroxycoumarin and pyridin-4-yl-methanol using HCl/dioxane to form the hydrochloric acid salt which is then purified by HPLC to afford the title compound as the trifluoroacetic acid salt (72.6 mg, 33.0%). $^1$H NMR (DMSO-d6, 300 MHz) δ 8.77 (2H, d, J=5.75 Hz), 7.94 (1H, d, J=2.5 Hz), 7.79 (2H, d, J=6 Hz), 7.75 (1H, dd, J=2.75, 8.75 Hz), 7.50 (1H, d, J=9Hz), 6.10 (1H, s), 5.56 (2H, s); MS (ESI, Pos.) calcd for $C_{15}H_{10}ClNO_3$ m/z [M+H]=288.0, found 288.1.

EXAMPLE 39

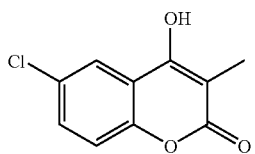

6-Chloro-4-hydroxy-3-methyl-1-benzopyran-2-one

Diethylcarbonate (27.2 mmol, 3.3 mL) is dissolved in 30 mL toluene, and NaH (16.3 mmol, 0.65 g of 60% dispersion) is added in portions. 5'-chloro-2'-hydroxy-propiophenone (5.4 mmol, 1.0 g) in 10 mL is dissolved in toluene and is added dropwise via an addition funnel to the above solution. The cloudy yellow-green mixture is heated to near reflux for 20 hrs then is cooled to ambient temperature. 1N NaOH (50 mL) is added and the mixture stirred at ambient temperature for 60 hrs. The layers are separated and the organic layer is washed with $H_2O$. The combined aqueous layers are washed with $Et_2O$ and the aqueous layer then acidified to pH 2 with conc. HCl. The resulting off-white precipitate is filtered, is washed with $Et_2O$, and is dried to afford the title compound (0.417 g, 37%). A second crop is obtained by refrigerating the filtrate (0.442 g, 39%). $^1$H NMR (DMSO-d6, 300 MHz) δ 11.50 (1H, br s), 7.88 (1H, d, J=2.5 Hz), 7.61 (1H, dd, J=2.62, 8.87 Hz), 7.40 (1H, d, J=8.87 Hz), 2.00 (3H, s); MS (ESI, Pos.) calcd for $C_{10}H_7ClO_3$ m/z [M+H]=211.0, found 210.9.

EXAMPLE 40

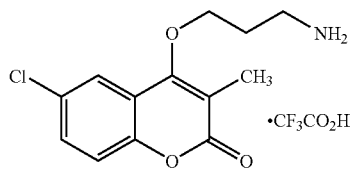

4-(3-Amino-propoxy)-6chloro-3-methyl-1-benzopyran-2-one Trifluoroacetic acid salt 6-chloro-4-hydroxy-3-methyl-1-benzopyran-2-one (1.0 mmol, 0.210 g) is suspended in 10 mL THF, and triphenylphosphine (1.05 mmol, 0.275 g) and (3-hydroxy-propyl)-carbamic acid tert-butyl ester (1.05 mmol, 0.184 g) are added. The reaction is cooled to 0° C. and DIAD (1.1 mmol, 0.222 g) is added dropwise at 0° C. The reaction is warmed to ambient temperature and is stirred overnight. The THF is removed under reduced pressure to give the Boc-protected intermediate. The Boc-protected intermediate is purified by reversed-phase HPLC and then is treated with neat TFA for 5 min. The TFA is removed in vacuo and $Et_2O$ is added to precipitate the product which is purified by reversed-phase HPLC to afford the title compound as the trifluoroacetic acid salt (116 mg, 30%). $^1$H NMR (DMSO-d6, 300 MHz) δ 7.79 (2H, br s), 7.73 (1H, d, J=2.2 Hz), 7.66 (1H, dd, J=2.8, 9 Hz), 7.48 (1H, d, J=8.8 Hz), 4.29 (2H, t, J=6.3 Hz), 3.03 (2H, m), 2.12 (2H, m), 2.09 (3H, s); MS (ESI, Pos.) calcd for $C_{13}H_{14}ClNO_3$ mrz [M+H]=268.1, found 268.1.

EXAMPLE 41

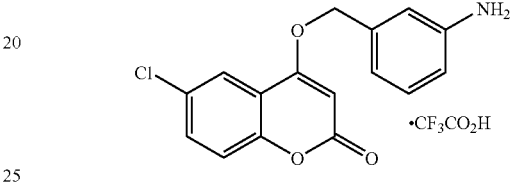

4-(3-Amino-benzyloxy)-6-chloro-1-benzopyran-2-one Trifluoroacetic acid salt

6-Chloro-4-hydroxycoumarin (0.939 mmol, 0.185 g), $PPh_3$ (0.986 mmol, 0.258 g), and (3-hydroxymethyl-phenyl)-carbamic acid tert-butyl ester (0.986 mmol, 0.219 g) are suspended in 10 mL of THF and the mixture is cooled to 0° C. DIAD (1.03 mmol, 0.203 mL) is added dropwise at 0° C., and then the reaction mixture is allowed to warm to ambient temperature and is stirred overnight. The Boc-protected intermediate is purified by HPLC then treated with neat TFA for 30 min at ambient temperature. The TFA is removed in vacuo and the crude material is purified by HPLC to afford the title compound as the trifluoroacetic acid salt (26.8 mg, 6.9%). %). $^1$H NMR (DMSO-d6, 300 MHz) δ 7.73 (2H, m), 7.48 (1H, m), 7.24 (1H, t), 6.94 (2H, m), 6.84 (1H, br d), 6.08 (1H, s), 5.29 (2H, s). MS (ESI, Pos.) calcd for $C_{16}H_{12}ClNO_3$ m/z [M+H]=302.1, found 302.1.

EXAMPLE 42

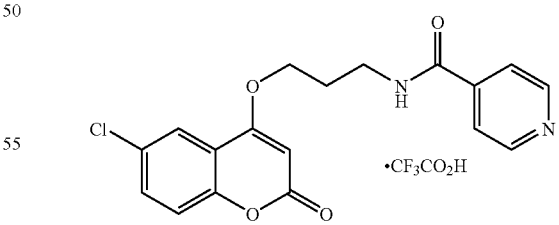

N-[3-(6-Chloro-2-oxo-2H-1-benzopyran-4-yloxy)-propyl]-isonicotinamide Trifluoroacetic acid salt The trifluoroacetic acid salt of 4-(3-amino-propoxy)-6-chloro-1-benzopyran-2-one (0.272 mmol, 0.10 g) is dissolved in 3 mL of DCM and is added enough DIEA to bring the pH to ~9 as measured by wet pH paper. Isonicotinoyl chloride hydrochloride is added (0.50 mmol, 0.089 g) and the reaction is stirred at ambient temperature overnight. The reaction mixture is evaporated under reduced pressure and the crude material is purified by HPLC to obtain the title compound as the trifluoroacetic acid salt (39 mg, 30%). $^1$H NMR (DMSO-d6, 300 MHz) δ 8.93 (1H, br t), 8.73 (2H, br d), 7.80 (2H, m), 7.76 (1H, d, J=2.5 Hz), 7.69 (1H, dd, J=2.5, 8.75 Hz), 7.45 (1H, d, J=8.75 Hz), 5.97 (1H, s), 4.31 (2H, t, J=5.75 Hz), 3.51 (2H, q, J=6.5 Hz), 2.11 (2H, m); MS (ESI, Pos.) calcd for $C_{18}H_{15}ClN_2O_4$ m/z [M+H]=359.1, found 359.1.

EXAMPLE 43

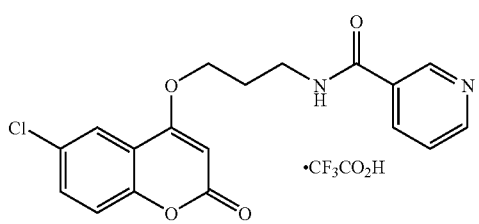

N-[3-(6-Chloro-2-oxo-2H-1-benzopyran-4-yloxy)-propyl]-nicotinamide Trifluoroacetic acid salt Is prepared via the method used for N-[3-(6-chloro-2-oxo-2H-1-benzopyran-4-yloxy)-propyl]-isonicotinamide from 4-(3-amino-propoxy)-6-chloro-1-benzopyran-2-one and nicotinoyl chloride hydrochloride to afford the title compound as the trifluoroacetic acid salt after HPLC purification (43.8 mg, 34%). $^1$H NMR (DMSO-d6, 300 MHz) δ 9.01 (1H, br d), 8.81 (1H, br t), 8.71 (1H, dd, J=1.5, 4.75 Hz), 8.23 (1H, m), 7.77 (1H, d, J=2.5 Hz), 7.69 (1H, dd, J=2.5, 8.75 Hz), 7.55 (1H, m), 7.46 (1H, d, J=8.75 Hz), 5.97 (1H, s), 4.31 (2H, t, J=6 Hz), 3.52 (2H, q, J=6.25 Hz), 2.12 (2H, m); MS (ESI, Pos.) calcd for $C_{18}H_{15}ClN_2O_4$ m/z [M+H]=359.1, found 359.1.

EXAMPLE 44

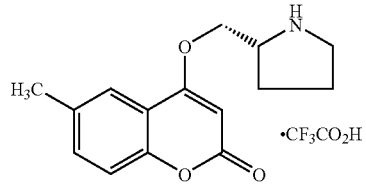

6-Methyl-4-((R)-pyrrolidin-2-ylmethoxy)-1-benzopyran-2-one Trifluoroacetic acid salt 6-methyl-4-hydroxy coumarin (0.851 mmol, 0.150 g), (R)-pyrrolidin-2-yl-methanol (0.936 mmol, 0.187 g), and PPh$_3$ (0.936 mmol, 0.245 g) is suspended in 10 mL THF. Cooled to 0° C. DIAD is added dropwise at 0° C. and then is stirred at ambient temperature overnight. Excess solvent is removed under reduced pressure and the crude material is treated with neat TFA at ambient temperature for 30 min. The TFA is removed in vacuo and the residue is purified by HPLC to obtain the title compound as the trifluoroacetic acid salt (13.0 mg, 5.9%). $^1$H NMR (DMSO-d6, 300 MHz) δ 9.10 (2H, br d), 7.75 (1H, br d), 7.51 (1H, dd, J=2, 8.5 Hz), 7.33 (1H, d, J=8.5 Hz), 5.97 (1H, s), 4.53 (1H, dd, J=3.5, 11.25 Hz), 4.30 (1H, m), 4.04 (1H, m), 3.27 (2H, buried under solvent peak), 2.40 (3H, s), 2.18 (1H, m), 1.98 (2H, m), 1.74 (1H, m); MS (ESI, Pos.) calcd for $C_{15}H_{17}NO_3$ m/z [M+H]=260.1, found 260.1.

EXAMPLE 45

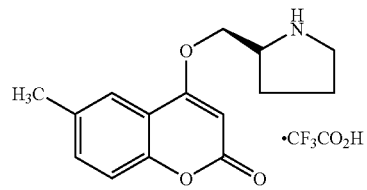

6-Methyl-4-((S)-pyrrolidin-2-ylmethoxy)-1-benzopyran-2-one Trifluoroacetic acid salt Is prepared via the method used for 6-methyl-4-((R)-pyrrolidin-2-ylmethoxy)-1-benzopyran-2-one from 6-methyl-4-hydroxycoumarin and (S)-pyrrolidin-2-yl-methanol to afford the title compound as the trifluoroacetic acid salt after HPLC purification (60.1 mg, 27%). $^1$H NMR (DMSO-d6, 300 MHz) δ 9.34 (1H, br s), 8.83 (1H, br s), 7.75 (1H, br d), 7.51 (1H, dd, J=1.75, 8.25 Hz), 7.33 (1H, d, J=8.5 Hz), 5.97 (1H, s), 4.53 (1H, dd, J=3.5, 11.25 Hz), 4.30 (1H, m), 4.05 (1H, m), 3.30 (2H, buried under solvent peak), 2.40 (3H, s), 2.17 (1H, m), 1.98 (2H, m), 1.75 (1H, m); MS (ESI, Pos.) calcd for $C_{15}H_{17}NO_3$ m/z [M+H]=260.1, found 260.1.

EXAMPLE 46

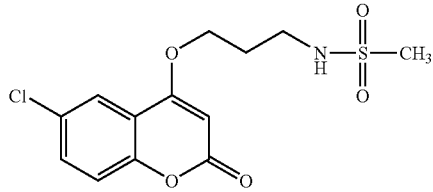

N-[3-(6-Chloro-2-oxo-2H-1-benzopyran-4-yloxy)-propyl]-methanesulfonamide 4-(3-Aminopropoxy)-6-chloro-1-benzopyran-2-one trifluoroacetate salt (0.272 mmol, 0.10 g) is suspended in 2 mL of DCM. DIEA (1.36 mmol, 0.236 mL) is added followed by methanesulfonyl chloride (0.543 mmol, 0.062 g) and the reaction is stirred at ambient temperature for 4 hrs. The solvent is removed under reduced pressure and the residue is redissolved and purified by HPLC to afford the title compound (21 mg, 23%); $^1$H NMR (DMSO-d6, 300 MHz) δ 7.80 (1H, d, J=2.6 Hz), 7.70 (1H, dd, J=2.5, 8.75 Hz), 7.45 (1H, d, J=8.87 Hz), 7.11 (1H, brt), 5.97 (1H, s), 4.28 (2H, t, J=6 Hz), 3.16 (2H, m), 2.91 (3H, s), 2.01 (2H, m); MS (ESI, Pos.) calcd for $C_{13}H_{14}ClNO_5S$ m/z [M+H]=332.0, found 331.9.

EXAMPLE 47

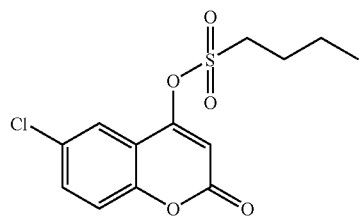

Butane-1-sulfonic acid
6-chloro-2-oxo-2H-1-benzopyran-4-yl ester

6-Chloro-4-hydroxycoumarin (0.455 mmol, 0.090 g) is suspended in 5 mL DCM. DIEA (1.37 mmol, 0.237 mL) is added and the reaction is cooled to 0° C. 1-Butanesulfonyl chloride (0.5 mmol, 64.8 µL) is dissolved in DCM is added and and the reaction is stirred at ambient temperature for 2 hrs. The DCM is removed under reduced pressure and the residue is redissolved in MeOH/H$_2$O then is purified by HPLC to afford the title compound (36.2 mg, 25%) $^1$H NMR (DMSO-d6, 300 MHz) δ 7.81 (2H, m), 7.56 (1H, d, J=8.75 Hz), 6.59 (1H, s), 3.99 (2H, m), 1.83 (2H, m), 1.46 (2H, m), 0.92 (3H, t, J=7.25 Hz); MS (ESI, Pos.) calcd for $C_{13}H_{13}ClO_5S$ m/z [M+H]=317.0, found 317.1.

EXAMPLE 48

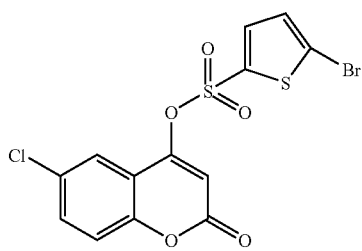

5-Bromo-thiophene-2-sulfonic acid 6-chloro-2-oxo-
2H-1-benzopyran-4-yl ester

6-Chloro-4-hydroxycoumarin (0.5 mmol, 0.099 g) is suspended in 5 mL of DCM, and enough DIEA is added to bring the pH to 9 as measured by pH paper. The solution is cooled to 0° C., and 5-bromo-thiophene-2-sulfonyl chloride (0.5 mmol, 0.13 g) is added. The solution is warmed to ambient temperature and is stirred 2 hrs. The solvent is removed under reduced pressure and the residue is triturated with Et$_2$O. The resulting solid is filtered, is washed with Et$_2$O, and is dried to afford the title compound (45 mg, 21%). $^1$H NMR (CDCl$_3$, 300 MHz) δ 7.65 (1H, d, J=4.25 Hz), 7.56 (2H, m), 7.29 (1H, d, J=8.75 Hz), 7.19 (1H, d, J=4.25 Hz), 6.48 (1H, s), MS (ESI, Pos.) calcd for $C_{13}H_6BrClO_5S_2$ m/z [M+H]=420.9, found 420.9.

EXAMPLE 49

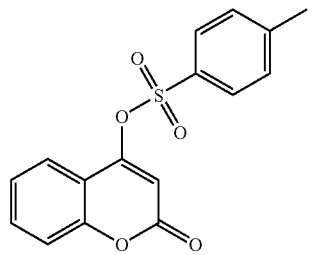

Toluene-4-sulfonic acid
2-oxo-2H-1-benzopyran-4-yl ester

A solution of 4-hydroxycoumarin (30.7 mmol, 4.98 g) and triethylamine (37.3 mmol, 5.2 mL) in THF (50 mL) is cooled to (0° C.). A THF solution (50 mL) of p-toluenesulfonyl chloride (33.5 mmol, 6.45 g) is added dropwise The mixture is stirred at 0° C. for 1.5 hrs., is filtered and the solid is washed with EtOAc. The filtrate is concentrated under reduced pressure and Et$_2$O is added. The resulting precipitate is filtered, is washed with Et$_2$O and is dried to afford the title compound (7.57 g, 79%); $^1$H NMR (CDCl$_3$, 300 MHz) δ 7.91 (2H, m), 7.61 (2H, m), 7.34 (4H, m), 6.31 (1H, s), 1.55 (3H, s); MS (ESI, Pos.) calcd for $C_{16}H_{12}O_5S$ m/z [M+H]=317.0, found 317.0.

EXAMPLE 50

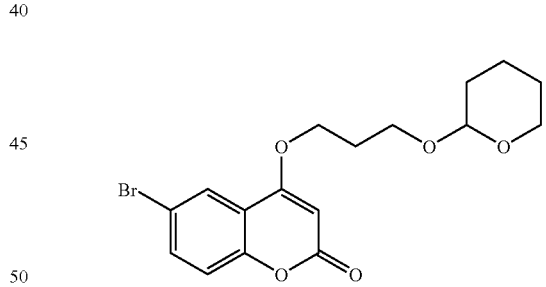

6-Bromo-4-[3-(tetrahydro-pyran-2-yloxy)-propoxy]-
1-benzopyran-2-one

6-Bromo-4-hydroxycoumarin (1.19 mmol, 0.287 g), K$_2$CO$_3$ (3.57 mmol, 0.493 g) and 2-3-(bromopropoxy)tetrahydro-2H-pyran (1.19 mmol, 0.264 g) is suspended in 10 mL of acetone, and is heated to 55° C. for 24 hrs at which time the reaction is not complete. Cs$_2$CO$_3$ (1.54 mmol, 0.5 g) and 5 mL of DMF are added and the reaction is heated for an additional 2 hrs. Twenty-five percent of the crude THP protected material is purified by HPLC to afford the title compound (70.8 mg, 62%); $^1$H NMR (CDCl$_3$, 300 MHz) δ 7.91 (1H, d, J=2.25 Hz), 7.82 (1H, dd, J=2.5, 9 Hz), 7.39 (1H, d, J=9 Hz), 5.98 (1H, s), 4.59 (1H, m), 4.31 (2H, t, J=6 Hz), 3.83

(1H, m), 3.72 (1H, m), 3.55 (2H, m), 2.09 (2H, m), 1.65 (2H, m), 1.45 (4H, m); MS (ESI, Pos.) calcd for $C_{17}H_{19}BrO_5$ m/z [M+H]=383.0, found 383.1.

EXAMPLE 51

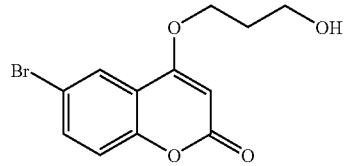

6-Bromo-4-(3-hydroxy-propoxy)-1-benzopyran-2-one

6-Bromo-4-[3-(tetrahydro-pyran-2-yloxy)-propoxy]-1-benzopyran-2-one (0.893 mmol, 0.342 g) is treated with 5 mL of 4:2:1 HOAc:THF:H$_2$O and is heated to 45° C. for 1 hr. The solvent is removed under reduced pressure and the residue is purified by HPLC to afford the title compound (105.8 mg, 60%); $^1$H NMR (DMSO-d6, 300 MHz) δ 7.90 (1H, d, J=2.5 Hz), 7.82 (1H, dd, J=2.25, 8.75 Hz), 7.39 (1H, d, J=8.75 Hz), 5.96 (1H, s), 4.29 (2H, t, J=6.25 Hz), 3.61 (2H, t, J=6 Hz), 1.97 (2H, m); MS (ESI, Pos.) calcd for $C_{12}H_{11}BrO_4$ m/z [M+H]=299.0, found 299.1.

EXAMPLE 52

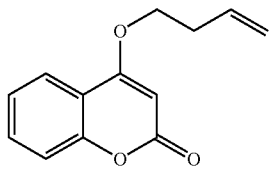

4-But-3-enyloxy-1-benzopyran-2-one

4-Hydroxycoumarin (10.93 mmol, 1.77 g), 4-bromo-1-butene (10.93 mmol, 1.48 g) and K$_2$CO$_3$ (33 mmol, 4.55 g) is suspended in 50 mL of acetone, and the reaction is heated to 55° C. for 2.5 days the reaction mixture is filtered and the filtrate is evaporated under reduced pressure. A small amount of the resulting solid is purified by column chromatography to afford an analytically pure sample of the title compound. $^1$H NMR (DMSO-d6, 300 MHz) δ 7.78 (1H, dd, J=1.5, 7.75 Hz), 7.66 (1H, m), 7.38 (2H, m), 5.93 (1H, m), 5.92 (1H, s), 5.20 (2H, m), 2.59 (2H, m), 2.50 (2H, m); MS (ESI, Pos.) calcd for $C_{13}H_{12}O_3$ m/z [M+H]=217.1, found 217.1.

EXAMPLE 53

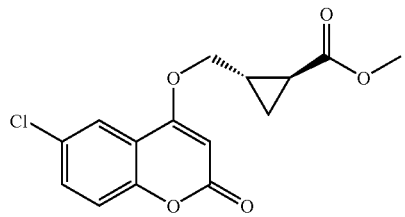

trans-2-(6-Chloro-2-oxo-2H-1-benzopyran-4-yloxymethyl)-cyclopropanecarboxylic acid methyl ester 6-chloro-4-hydroxycoumarin (5.09 mmol, 1.0 g) is dissolved in 80 mL of DMF, and Cs$_2$CO$_3$ (7.63 mmol, 2.49 g), and trans-2-methanesulfonyloxymethyl-cyclopropanecarboxylic acid methyl ester (6.14 mmol, 1.28 g) are added. The reaction is heated to 100° C. for 5 hrs, a further 0.2 eq of the mesylate is added, and heating is continued for an additional 2 hrs. After cooling to ambient temperature, the DMF is removed in vacuo. The residue is dissolved in EtOAc and is washed with H$_2$O. The organic layer is dried over MgSO$_4$, is filtered, and the EtOAc is removed under reduced pressure to afford a yellow solid which is chromatographed on SiO$_2$ (35 g) using DCM as the eluent to afford the title compound as a white solid (0.98 g, 62%). $^1$H NMR (DMSO-d6, 300 MHz) δ 7.75 (2H, m), 7.45 (1H, d), 5.97 (1H, s), 4.22 (2H, m), 3.65 (3H, s), 1.90 (2H, m), 1.19 (2H, m); MS (ESI, Pos.) calcd for $C_{15}H_{13}ClO_5$ m/z [M+H]=309.0, found 309.0.

EXAMPLE 54

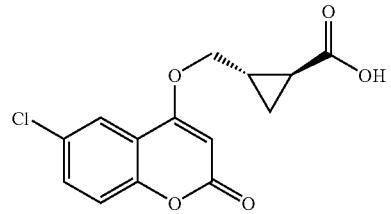

trans-2-(6-Chloro-2-oxo-2H-1-benzopyran-4-yloxymethyl) cyclopropanecarboxylic acid trans-2-(6-Chloro-2-oxo-2H-1-benzopyran-4-yloxymethyl) cyclpropanecarboxylic acid methyl ester (3.19 mmol, 0.98 g) is dissolved in THF (15 mL). A solution of LiOH (5.58 mmol, 0.134 g) in 5 mL of H$_2$O is added to the reaction mixture and it is stirred overnight at ambient temperature. An additional 0.5 eq. LiOH is added and the mixture is stirred 1 hr. The solution is concentrated, the reaction mixture is diluted with H$_2$O, and then is extracted with Et$_2$O to remove any unreacted starting material. The aqueous layer is acidified with 3N HCl and the resulting precipitate is extracted into DCM. The DCM layer is dried (MgSO4), filtered, and evaporated to afford the title compound as a white solid (0.367 g, 40%). $^1$H NMR (300 MHz) 12.25 (1H, brs), 7.74 (1H, m), 7.70 (1H, d, J=2.5 Hz), 7.46 (1H, d, J=8.75 Hz), 6.99 (1H, s), 4.20 (2H, m), 1.85 (1H, m), 1.7 (1H, m), 1.18 (1H, m), 1.05 (1H, m); MS (ESI, Pos.) calcd for $C_{14}H_{11}ClO_5$ m/z [M+H]=295.0, found 295.1.

EXAMPLE 55

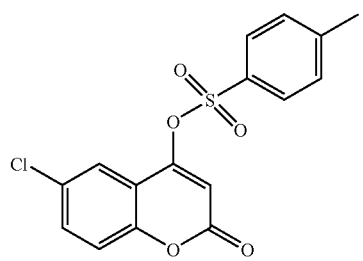

Toluene-4-sulfonic acid 6-chloro-2-oxo-2H-1-benzopyran-4-yl ester

6-Chloro-4-hydroxycoumarin (25.4 mmol, 5.0 g) is suspended in DCM (50 mL) and pyridine (63.3 mmol, 5.1 mL) is added. The mixture is cooled in an ice bath and p-toluenesulfonyl chloride (26.8 mmol, 5.1 g) is added. The ice bath is removed and the compound slowly dissolves and a solid is deposited (pyridine HCl). After 1 hr the mixture is transferred to a separatory funnel, HCl (2 M) is added, and a solid is formed. The organic layer is removed and the solid-containing aqueous layer is filtered to remove the precipitate. The filtrate is washed with DCM and the combined organic layers are washed with $H_2O$, NaHCO$_3$ (sat.), $H_2O$, and brine. The extract is then dried over MgSO$_4$ and is evaporated. The residue is triturated with Et$_2$O to give the title compound (8.0 g, 90%) as a cream solid. $^1$H NMR (CDCl$_3$, 400 MHz) δ 7.91 (2H, d, J=8 Hz), 7.54 (1H, d, J=2 Hz), 7.51 (1H, dd, J=2, 9 Hz), 7.42 (2H, d, J=8 Hz), 7.26 (1H, d, J=9 Hz), 6.38 (1H, s), 2.49 (3H, s); LCMS (MeCN—H$_2$O, Luna 3µC18(2) 30×4.6 mm; MS (ESI, Pos.) calcd for $C_{16}H_{11}ClO_5S$ m/z [M+H]=351 found [no mass ion detected].

EXAMPLE 56

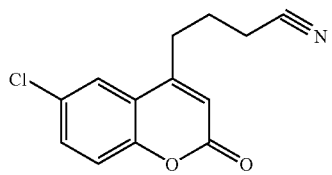

4-(6-Chloro-2-oxo-2H-1-benzopyran-4-yl)-butyronitrile

Toluene-4-sulfonic acid 6-chloro-2-oxo-2H-1-benzopyran-4-yl ester (1.05 g, 3 mmol) is dissolved in THF (30 mL) under nitrogen and [P(o-tolyl)$_3$]$_2$PdCl$_2$ (120 mg, 0.15 mmol) is added 3-cyanopropylzinc bromide (9 mL of a 0.5 M solution in THF, 4.5 mmol) is added and the resulting yellow solution is stirred at 60° C. for 2 hrs. Silica gel is added to the dark red reaction mixture, which is concentrated in vacuo and purified by flash column chromatography eluting with CH$_2$Cl$_2$ and gradually increasing polarity to 1% MeOH—CH$_2$Cl$_2$ to give a residue which is triturated with Et$_2$O to give the title compound (0.54 g, 73%) as a cream solid. $^1$H NMR (DMSO-d6, 400 MHz) d 7.92 (1H, d, J=2 Hz), 7.68 (1H, dd, J=9, 2 Hz), 7.46 (1H, d, J=9 Hz), 6.47 (1H, s), 2.90 (2H, t, J=7 Hz), 2.63 (2H, t, J=7 Hz), 1.94 (2H, q, J=7 Hz). LCMS (MeCN—H2O, MeCN—H2O, Luna 3 m C18(2) 30×4.6mm; (ESI Pos.) calcd for $C_{13}H_{10}ClNO_2$ m/z [M+H]=248; found [no mass ion detected].

EXAMPLE 57

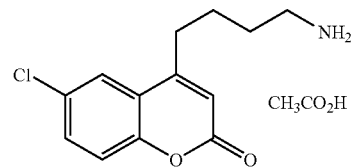

4-(4-Aminobutyl)6-chloro-1-benzopyran-2-one, Acetic acid salt 4-(6-Chloro-2-oxo-2H-1-benzopyran-4-yl)-butyronitrile (200 mg, 0.8 mmol) is suspended in EtOH (20 mL) and a spatula of Raney nickel is added. The mixture is placed under a hydrogen atmosphere and is stirred vigorously at 60° C. for 1 hr. The resulting suspension is filtered through Hyflo and concentrated in vacuo. The residue is dissolved in EtOH (5 mL) and treated with HCl (1 M in Et$_2$O). The resulting solid (128 mg) is purified by flash column chromatography eluting with CH$_2$Cl$_2$:MeOH:AcOH:H$_2$O (240:60:6:4) to give the title compound (85 mg, 27%) as a white solid. $^1$H NMR (DMSO-d$_6$, 400 MHz) δ 7.93 (1H, d, J=2.5 Hz), 7.68 (1H, dd, J=9, 2.5 Hz), 7.46 (1H, d, J=9 Hz), 6.44 (1H, s), 5.5-4.0 (3H, br s), 2.83 (2H, t, J=7 Hz), 2.68 (2H, m), 1.78 (3H, s), 1.65 (2H, m), 1.54 (2H, m); LCMS MeCN—H$_2$O, Luna 3µ C18(2) 30×4.6mm; calcd for $C_{13}H_{14}ClNO_2$ m/z [M+H]=252, found [no mass ion detected].

EXAMPLE 58

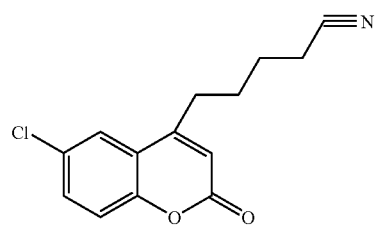

4-(6-Chloro-2-oxo-2H-1-benzopyran-4-yl)-pentanenitrile

Is prepared via the method used for 4-(6-Chloro-2-oxo-2H-1-benzopyran-4-yl)-butyronitrile except 4-cyanobutylzinc bromide is used instead of 3-cyanopropylzinc bromide.

EXAMPLE 59

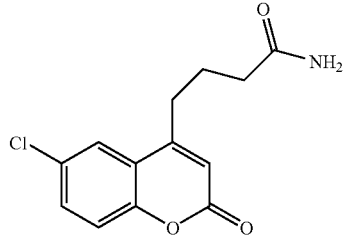

4-(6-Chloro-2-oxo-2H-1-benzopyran-4-yl)-butyramide 4-(6-Chloro-2-oxo-2H-1-benzopyran-4-yl)-butyronitrile (100 mg, 0.4 mmol) is dissolved in conc. $H_2SO_4$ (2 mL) and is stirred for 4 hrs. Ice and then $H_2O$ (20 mL) is added to the reaction mixture, and the resulting precipitate is filtered and is washed with $H_2O$ and $Et_2O$. The solid is dried in vacuo to give the title compound (100 mg, 93%) as a white solid. $^1$H NMR (DMSO-d6, 400 MHz) δ 7.98 (1H, d, J=2 Hz), 7.68 (1H, dd, J=2, 9 Hz), 7.47 (1H, d, J=9 Hz), 7.32 (1H, broad s), 6.83 (1H, broad s), 6.43 (1H, s), 2.79 (2H, t, J=7 Hz), 2.20 (2H, t, J=7 Hz), 1.82 (2H, q, J=7 Hz); LCMS (MeCN—$H_2O$, Luna 3μ C18(2) 30×4.6 mm) m/z (ES, Pos) calc. for $C_{13}H_{12}ClNO_3$ m/z [M+H]=266, found 266.

EXAMPLE 60

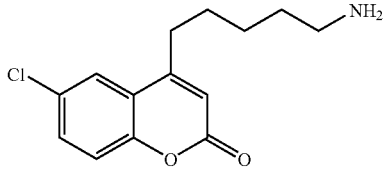

4-(5-Amino-pentyl)-6-chloro-1-benzopyran-2-one 5-(6-Chloro-2-oxo-2H-1-benzopyran-4-yl)-pentanenitrile (0.76 mmol, 0.200 g) is suspended in EtOH (20 mL), Raney Nickel (spatula full) is added and the mixture placed under $H_2$. The mixture is stirred at 60° C. for 1 hr; and TLC indicates no starting material remained. The resulting mixture is filtered through Hyflo and is evaporated to leave a yellow gum. The gum is dissolved in EtOH (5 mL) and is treated with 1 M HCl in $Et_2O$ (5 mL). No solid is deposited. The solvent is evaporated in vacuo and the residue is purified by flash column chromatography using $CH_2Cl_2$:MeOH:AcOH:$H_2O$ 240:30:3:2 as eluent, giving the title compounds as an off-white solid (80 mg) in 39% yield. $^1$H NMR (DMSO-d6): δ 7.89 (1H, d, J=2.4 Hz), 7.68 (1H, dd, J=8.8 Hz, 2.4 Hz), 7.46 (1H, d, J=8.8 Hz), 6.43 (1H, s), 2.82 (2H, t, J=7.4 Hz), 2.77 (2H, t, 7.4 Hz), 1.67-1.57 (4H, m), 1.47-1.44 (m, 2H). LCMS (MeCN—$H_2O$, Luna 3μ C18(2) 30×4.6 mm) m/z (ESI, Pos.) calcd for $C_{14}H_{16}ClNO_2$ m/z [M+H]=266.1, found 266.1.

EXAMPLE 61

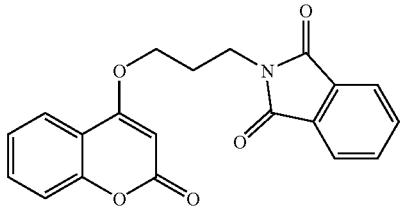

2-[3-(2-Oxo-2H-1-benzopyran-4-yloxy)-propyl]-isoindole-1,3-dione 4-hydroxycoumarin (6.17 mmol, 1.0 g), $PPh_3$ (6.48 mmol, 1.70 g), and 2-(3-hydroxy-propyl)-isoindole-1,3-dione (6.48 mmol, 1.33 g) is disolved in 20 mL THF and is cooled to 0° C. DIAD (6.79 mmol, 1.33 mL) is added dropwise at 0° C. A precipitate is formed immediately and the reaction mixture thickens. The precipitate is filtered, is washed with $Et_2O$ and is dried to afford the title compound (1.62 g, 75%). $^1$H NMR (DMSO-d6, 300 MHz) δ 7.82 (4H, m), 7.61 (2H, m), 7.37 (1H, m), 7.21 (1H, m), 5.83 (1H, s), 4.28 (2H, t, J=5.75 Hz), 3.83 (2H, t, J=6.25 Hz), 2.19 (2H, m); MS (ESI, Pos.) calcd for $C_{20}H_{15}NO_5$ m/z [M+H]=350.1, found 350.1.

What is claimed is:

1. A compound of formula (I):

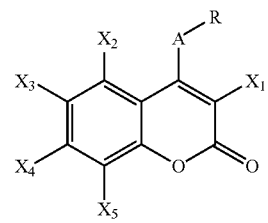

wherein:
A is O,
R is selected from the group consisting of $(CH_2)_nNR_1R_2$, wherein $R_1$ and $R_2$ are the same or different and are selected from the group consisting of hydrogen, C(=NH)$NH_2$ and $C_1$-$C_6$ alkyl,
n is an integer of from 2-5;
$X_1$ is hydrogen
$X_2$ is hydrogen;
$X_3$ is halogen,
$X_4$ is hydrogen; and
$X_5$ is hydrogen with the proviso that when n is 2, $R_1$ and $R_2$ are not both hydrogen or both ethyl and $X_3$ chlorine,
and the pharmaceutically acceptable salts and optical isomers thereof.

2. The compound according to claim 1 wherein:
A is O;
R is $(CH_2)_nNR_1R_2$, and
$X_3$ is halogen.

3. The compound according to claim 2 wherein $R_1R_2$ are selected from the group consisting of hydrogen, $C_{1-6}$alkyl, and $C(=NH)NH_2$.

4. The compound according to claim 3 wherein $X_3$ is selected from the group consisting of bromine and chlorine.

5. The compound according to claim 4 wherein the halogen is chlorine.

6. The compound according to claim 1 selected from the group consisting of:
- 6-Chloro-4-(3-aminopropoxy)-1-benzopyran-2-one,
- 6-Chloro-4-(3-methylamino-propoxy)-1-benzopyran-2-one,
- 4-(2-Amino-ethoxy)-6-chloro-1-benzopyran-2-one,
- 4-(3-Amino-propoxy)-6-bromo-1-benzopyran-2-one,
- 4-(3-Amino-propoxy)-6-fluoro-1-benzopyran-2-one,
- 6-Chloro-4-(3-dimethylamino-propoxy)-1-benzopyran-2-one,
- N-[3-(6-Chloro-2-oxo-2H-1-benzopyran-4-yloxy)-propyl]-guanidine,
- N-[3-(6-Chloro-2-oxo-2H-1-benzopyran-4-yloxy)-propyl]-acetamide,
- 4-(5-Amino-pentyloxy)-6-chloro-1-benzopyran-2-one.

7. A pharmaceutical composition comprising an effective amount of a compound according to claim 6 and a pharmaceutical acceptable carrier.

* * * * *